US010070937B2

(12) United States Patent
Barley et al.

(10) Patent No.: US 10,070,937 B2
(45) Date of Patent: *Sep. 11, 2018

(54) VISUALIZATION APPARATUS

(71) Applicant: KONINKLIJKE PHILIPS N.V., Eindhoven (NL)

(72) Inventors: Maya E Barley, Guildford (GB); Szabolcs Deladi, Veldhoven (NL); Erik Godefridus Antonius Harks, Rijen (NL); Jan Frederik Suijver, Dommelen (NL); Mischa Megens, Millbrae, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/728,572

(22) Filed: Oct. 10, 2017

(65) Prior Publication Data
US 2018/0064504 A1 Mar. 8, 2018

Related U.S. Application Data

(62) Division of application No. 13/321,580, filed as application No. PCT/IB2010/051919 on May 3, 2010, now Pat. No. 9,808,323.

(30) Foreign Application Priority Data

Jun. 4, 2009 (EP) ..................................... 09161938

(51) Int. Cl.
G09G 5/00 (2006.01)
A61B 90/00 (2016.01)
(Continued)

(52) U.S. Cl.
CPC .......... *A61B 90/36* (2016.02); *A61B 18/1492* (2013.01); *A61B 34/20* (2016.02);
(Continued)

(58) Field of Classification Search
CPC .................................................. G06F 17/30716
See application file for complete search history.

(56) References Cited

U.S. PATENT DOCUMENTS 5,409,000 A 4/1995 Imran
5,904,651 A 5/1999 Swanson et al.
(Continued)

FOREIGN PATENT DOCUMENTS

WO 2007100263 A1 9/2007

OTHER PUBLICATIONS

Bamber, J.C., "Ultrasound elasticity imaging: definition and technology", European Radiology, 1999, vol. 9, No. 3, p. S327-S330.
(Continued)

*Primary Examiner* — Phi Hoang

(57) ABSTRACT

The invention relates to a visualization apparatus for visualizing a quality of applying energy to an object. The quality of applying energy at a location on the object (3) is visualized based on a) a provided image of the object and b) a provided quality value which is a depth value indicative of the depth to which the applied energy has altered the object, representing the quality of applying energy to the object at the location on the object (3), wherein a visual property assigning unit (9) assigns a visual property to the location depending on the quality value and a display (10) displays the provided image and the assigned visual property at the location on the object shown in the image as a transmural region calculated using depth value(s) with respect to a wall of the object. In general a person who applies energy to the object is focused on the location at which energy is applied.
(Continued)

Since quality information is shown at the location on which the person is already focused, the quality dependent information can easily be absorbed by the person.

10 Claims, 18 Drawing Sheets

(51) Int. Cl.
    *A61B 17/00*     (2006.01)
    *A61B 34/20*     (2016.01)
    *A61B 18/14*     (2006.01)

(52) U.S. Cl.
    CPC ............... *A61B 2017/00106* (2013.01); *A61B 2090/062* (2016.02); *A61B 2090/065* (2016.02); *A61B 2090/376* (2016.02)

(56) References Cited

U.S. PATENT DOCUMENTS

| | | | |
|---|---|---|---|
| 5,983,126 A | 11/1999 | Wittkampf | |
| 6,024,703 A | 2/2000 | Zanelli | |
| 6,129,722 A * | 10/2000 | Ruiz | A61F 9/008 351/212 |
| 6,241,725 B1 * | 6/2001 | Cosman | A61B 18/1477 600/41 |
| 6,246,896 B1 | 6/2001 | Dumoulin et al. | |
| 6,575,969 B1 | 6/2003 | Rittman, III et al. | |
| 7,001,383 B2 | 2/2006 | Keidar | |
| 7,306,593 B2 | 12/2007 | Keidar et al. | |
| 8,182,433 B2 | 5/2012 | Leo et al. | |
| 2004/0073111 A1 | 4/2004 | Poland et al. | |
| 2005/0283074 A1 | 12/2005 | Jackson et al. | |
| 2006/0122587 A1 | 6/2006 | Sharareh | |
| 2007/0232909 A1 | 10/2007 | Hughes et al. | |
| 2008/0033418 A1 * | 2/2008 | Nields | A61B 18/18 606/27 |
| 2008/0300589 A1 | 12/2008 | Paul et al. | |
| 2008/0317319 A1 * | 12/2008 | Lautenschlager | A61B 90/36 382/131 |
| 2009/0105585 A1 | 4/2009 | Wang et al. | |
| 2009/0248014 A1 | 10/2009 | Shachar et al. | |
| 2010/0050927 A1 * | 3/2010 | Sultan | B60K 37/02 116/288 |
| 2010/0113966 A1 | 5/2010 | Spruce | |
| 2012/0004547 A1 | 1/2012 | Harks et al. | |

OTHER PUBLICATIONS

Lee, S-L, et al. "From medical images to minimally invasive intervention: Computer assistance for robotic surgery", Computerized Medical Imaging and Graphics (2009), doi: 10.1016/j.compmedimg.2009,07.007.

Grimson, W.E.L. et al. "An automatic registration method for frameless stereotaxy, image guided surgery and enhanced reality visualization", IEEE Transactions on Medical Imaging, vol. 15, No. 2, Apr. 1996.

Ohnishi, M. et al. "Dynamic analysis of laser ablation of biological tissue using a real-time OCT", Proc. of SPIE vol. 7175, 717513, 2009.

* cited by examiner

VISUALIZATION APPARATUS

CROSS REFERENCE TO RELATED APPLICATION

This is a divisional of prior application Ser. No. 13/321,580 filed Jan. 16, 2012.

FIELD OF THE INVENTION

The invention relates to a visualization apparatus and visualization method for visualizing a quality of applying energy to an object. The invention relates further to an energy application apparatus and energy application method for applying energy to an object and to corresponding computer programs.

BACKGROUND OF THE INVENTION

US 2006/0122587 A1 discloses an apparatus for the evaluation of tissue ablation. The apparatus comprises a broadband light and/or laser light illumination source that delivers light to a site where a lesion is being formed. Scattered light is collected from the ablated tissue and evaluated to obtain qualitative information regarding the newly formed lesion. In particular, the collected light is translated into electrical signals and the electrical signals are provided to a computer for generating a graphical display or other information regarding parameters of the lesion such as lesion formation, depth of penetration of the lesion, cross-sectional area of the lesion in the tissue, formation of char during the ablation, recognition of char from non-charred tissue, et cetera.

SUMMARY OF THE INVENTION

It is an object of the present invention to provide a visualization apparatus for visualizing a quality of applying energy to an object, wherein information regarding the quality of applying energy to an object is visualized such that the information is readily absorbable by a person who applies energy to the object.

In a first aspect of the present invention a visualization apparatus for visualizing a quality of applying energy to an object is presented, wherein the visualization apparatus is adapted to visualize the quality of applying energy at a location on the object based on a provided image of the object and a provided quality value representing the quality of applying energy to the object at the location on the object, wherein the visualization apparatus comprises:

a visual property assigning unit for assigning a visual property to the location depending on the quality value, a display for displaying the provided image and the assigned visual property at the location on the object shown in the image.

Since the quality is visualized by displaying the assigned visual property at the location on the object shown in the image at which the energy is applied to the object, the same display can be used for showing the location at which energy is applied and for indicating the quality of applying energy to the object. It may therefore be possible to seamlessly blend the visualization of the quality of applying energy to the object with a standard visualization system comprising a display showing the object and the location at which energy is applied to the object. Moreover, in general a person who applies energy to the object is focused on the location at which energy is applied. Since quality information is shown at the location on which the person is already focused, the quality dependent information can easily be absorbed by the person.

The object is preferentially a heart of a human being or of an animal and energy is preferentially applied for ablating tissue of the heart. The object can also be another object like another organ or a technical object.

The energy is preferably applied within the heart by using an ablation catheter. The energy is therefore preferentially applied at a location on an inner wall of the heart.

The image is preferably a three-dimensional image of the object generated by using an imaging modality like a computed tomography system, an X-ray imaging system, in particular, for performing a rotational angiography, a magnetic resonance imaging system, a nuclear imaging system, an ultrasound imaging system, et cetera. The three-dimensional information can also be obtained by impedance, magnetic or electromagnetic-based tracking of the position of a catheter. At several locations on the object properties of the object, in particular, electrical properties can be measured and indicated on the image of the object for generating an electroanatomic map of the object. The provided image can therefore be an electroanatomic map of the object.

The visual property assigning unit is preferably adapted to assign a color and/or an intensity as the visual property. The display can be adapted to show several locations on the object, at which energy has already been applied and/or is actually applied, wherein at these locations the respective visual property is shown, which indicates the qualities at the respective locations to which the applied energy has altered the object.

It is preferred that the quality value is a depth value being indicative of the depth to which the applied energy has altered the object at the location. The depth to which the applied energy has altered the object is preferentially an ablation depth.

It is further preferred that the depth value is provided with respect to a thickness of a wall of the object. For example, the provided depth value can be indicative of a degree of transmurality and the visual property assigning unit can be adapted to assign the visual property depending on the degree of transmurality. For example, if the degree of transmurality is 100 percent, a certain color is assigned, for instance green. This allows the person to easily recognize whether a wall of the object has been altered by the energy completely or not. For example, if energy is applied to the heart of a person during an ablation procedure, the person can easily recognize the ablation depth with respect to the thickness of the wall of the heart. This allows the person to apply energy to the wall such that the ablation depth is substantially equal to the wall thickness and not larger or smaller, even if energy is applied at different locations at which the wall thickness is different.

It is further preferred that the object has a wall to which the energy is applied, wherein the visualization apparatus comprises a transmural region calculation unit for calculating a transmural region of the object based on the provided depth value and wherein the display is adapted to show the calculated transmural region on the image of object.

Preferentially, depth values are provided for several locations, wherein these depth values and the locations are used for calculating one or several transmural regions. Prior art on lesion formation dynamics can also be used for calculating the one or several transmural regions. The transmural region is preferentially indicated by showing a line surrounding the transmural region on the object. If a person wants to create a desired transmural region, the person can see on the display whether the actually obtained transmural region corresponds already to the desired region, and the person can recognize the locations, at which energy has to be applied, in order to obtain the desired transmural region. Since also the information regarding the actual transmural region is shown on the display, also this information can easily be absorbed by the person who applies energy to the object.

It is further preferred that energy is applied to the object by using an energy application element and wherein the quality value is a contact value being indicative of a degree of contact between the energy application element and the object. By visualizing the degree of contact at the location, at which energy is applied, also this quality information can easily be absorbed by a person who intends to apply energy to the object or who already applies energy to the object. The visual property assigning unit can be adapted to assign two visual properties to the location depending on a depth value and the contact value. For example, a first visual property can be assigned to the location depending on the depth value and a second visual property can be assigned to the location depending on the contact value. In an embodiment, the first visual property is the color and the second visual property is the intensity or vice versa. This allows the visualization apparatus to display two quality values at the location at which energy is applied. The visualization apparatus can be adapted to assign a visual property to the location depending on the quality value before energy is applied and/or during the application of energy and/or after energy has been applied. Correspondingly, the visualization apparatus can be adapted to display the provided image and the assigned visual property at the location on the object before energy is applied and/or during energy is applied and/or after energy has been applied.

It is preferred that the provided image of the object is an anatomic map, in particular, an electroanatomic map, of the object, wherein the display is adapted to display the assigned visual property at the location on the anatomic map. The anatomic map, in particular, the electroanatomic map, can guide a person to appropriate locations for applying energy to the object. Since the visual property indicating the quality of applying energy to the object is shown on the anatomic map of the object, both, the anatomic information, in particular, the electroanatomic information, and the quality information, can easily be absorbed by the person.

It is preferred that the visualization apparatus further comprises a gauge element shown on the display, wherein the gauge element is adapted to indicate a relation between a visual property and the quality value, in particular, the depth value. For example, the gauge element can indicate which color belongs to which quality value, in particular, to which degree of transmurality. Or the gauge element can indicate which color belongs to which absolute ablation depth.

It is further preferred that the quality value is a depth value being indicative of the depth to which the applied energy has altered the object at the location, wherein the gauge element comprises a marker indicating the depth to which the applied energy has altered the object based on depth value.

The depth value can be indicated as absolute value, for example, in millimeters, or the depth value can be indicated in relative values, for example, in degree of transmurality. For indicating the depth value the gauge can comprise a line, in particular, a black line, which moves in accordance with the changing depth at the location as the marker. Since also the gauge element is shown on the display, also the information provided by the gauge element can easily be absorbed by the person who applies energy to the object.

It is further preferred that the quality value is repeatedly provided during applying energy to the object, wherein the visual property assigning unit is adapted to repeatedly assign a visual property to the location depending on the respective actually provided quality value and wherein the display is adapted to repeatedly display the provided image and the respective actually assigned visual property at the location on the object shown in the image. This allows indicating the respective quality information to which the applied energy has influenced the object in realtime while applying energy at the location.

In a further aspect of the present invention an energy application apparatus for applying energy to an object is presented, wherein the energy application apparatus comprises:
  an image providing unit for providing an image of the object,
  an energy application element for applying the energy to the object at a location,
  a localization unit for localizing the energy application element at the location,
  a quality value determining unit for determining a quality value at the location on the object, wherein the quality value represents the quality of applying energy to the object at the location,
  the visualization apparatus as defined in claim 1.

The image providing unit is preferentially adapted to provide a two-dimensional or three-dimensional image of the object. The image providing unit can be a storing unit in which the image is stored already or a receiving unit for receiving the image via a wireless or wired data connection. The image providing unit can also be an imaging modality like a computed tomography system, a magnetic resonance imaging system, a nuclear imaging system, an ultrasound imaging system, et cetera. The image providing unit can also be a mapping system providing image information by impedance, magnetic or electromagnetic-based tracking of the position of a catheter. The object shown in the image can be provided with measured properties of the object at the locations of the object at which these properties have been measured. These properties are preferentially electrical properties and the resulting image is preferentially an electroanatomic map.

The energy application element is preferentially a tip of a catheter, which can be introduced into the object for applying energy to an inner wall of the object. In particular, the catheter is an ablation catheter for performing an ablation procedure within a heart of a human being or of an animal.

It is further preferred that the localization unit is adapted to use at least one of the following techniques for localizing the energy application element: electromagnetic tracking, impedance localization, magnetic resonance localization, X-ray localization, optical shape sensing and ultrasound localization.

It is preferred that the quality value determining unit is adapted to determine the depth of a lesion created by applying the energy at the location and/or the degree of contact between the energy application element and the object. It is further preferred that the energy application apparatus comprises a sensing unit for generating a sensing signal being indicative of a property of the object at the location, wherein the quality value determining unit is adapted to determine the quality value, in particular, the depth value and/or the contact value, depending on the generated sensing signal. The sensing unit is preferentially at least one of a magnetic resonance unit and an ultrasound unit.

In a further aspect of the present invention a visualization method for visualizing a quality of applying energy to an object is presented, wherein the visualization method is adapted to visualize the quality of applying energy at a location on the object based on a provided image of the object and a provided quality value at the location on the object, the quality value representing the quality of applying energy to the object at the location on the object, wherein the visualization method comprises:

assigning a visual property to the location depending on the quality value, displaying the provided image and the assigned visual property at the location on the object shown in the image.

In a further aspect of the present invention an energy application method for applying energy to an object is presented, wherein the energy application method comprises:

providing an image of the object, localizing an energy application element for determining a location of the energy application element, applying energy to the object at the location by using the localized energy application element, determining a quality value at the location on the object, wherein the quality represents the quality of applying energy to the object at the location, visualizing the effect of applying energy to the object as defined in claim 12.

In a further aspect of the present invention a computer program for visualizing an effect of applying energy to an object is presented, wherein the computer program comprises program code means for causing a visualization apparatus as defined in claim 1 to carry out the steps of the visualization method as defined in claim 12, when the computer program is run on a computer controlling the visualization apparatus.

In a further aspect of the present invention a computer program for applying energy to an object is presented, wherein the computer program comprises program code means for causing an energy application apparatus as defined in claim 10 to carry out the steps of the energy application method as defined in claim 13, when the computer program is run on a computer controlling the energy application apparatus.

It shall be understood that the visualization apparatus of claim 1, the energy application apparatus of claim 10, the visualization method of claim 12, the energy application method of claim 13 and the computer programs of claims 14 and 15 have similar and/or identical preferred embodiments, in particular, as defined in the dependent claims. It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF THE EMBODIMENTS

Figure 1:
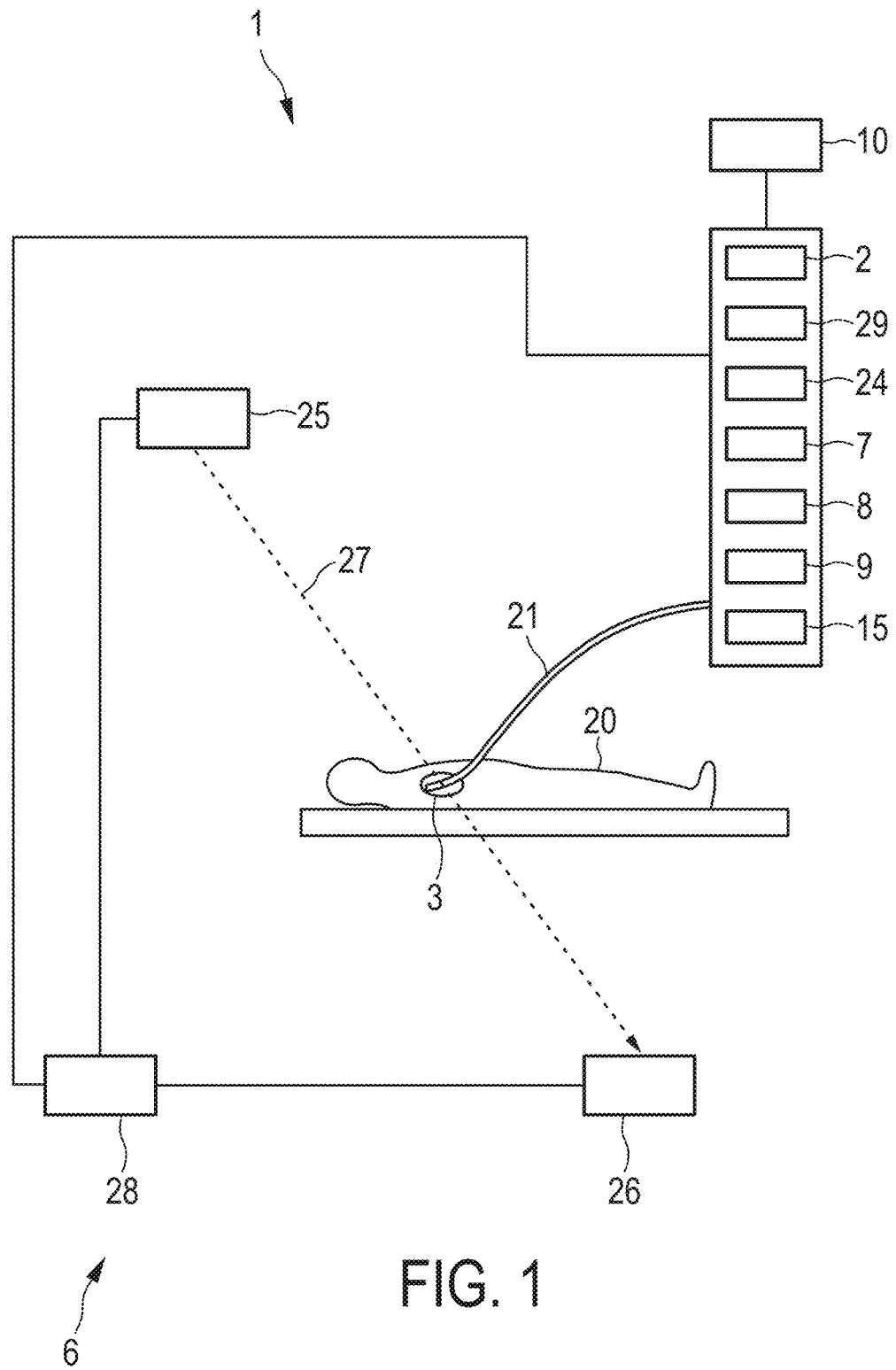
FIG. 1 shows schematically and exemplarily an embodiment of an energy application apparatus for applying energy to an object.
Figure 2:
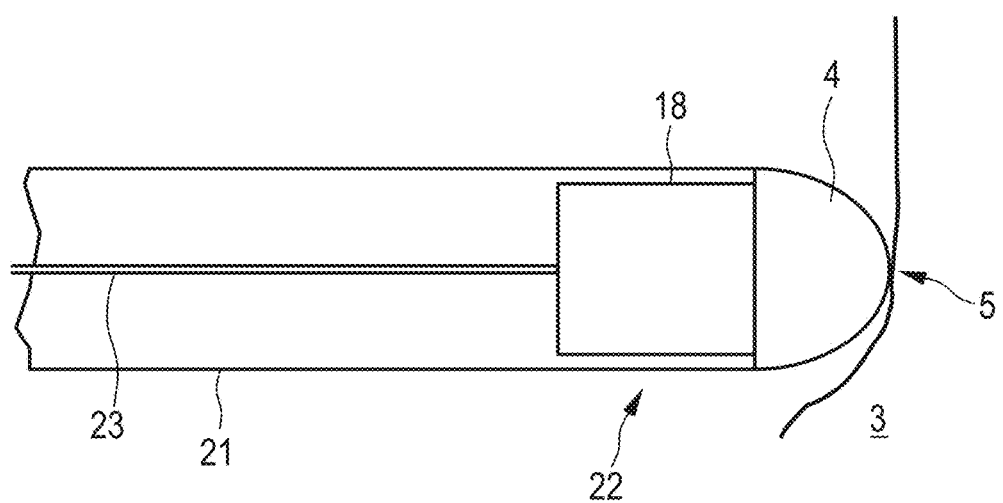
FIG. 2 shows schematically and exemplarily a catheter tip of the energy application apparatus.

FIG. 1 shows schematically and exemplarily an energy application apparatus 1 for applying energy to an object. The energy application apparatus 1 comprises an image providing unit 2 for providing an image of the object 3 being, in this embodiment, a heart of a person 20. The energy application apparatus 1 further comprises a catheter 21 for applying energy to an inner wall of the heart 3. The tip 22 of the catheter 21 is schematically and exemplarily shown in FIG. 2. The catheter tip 22 comprises an ablation electrode 4 for applying the energy to the wall of the heart 3 at a location 5. The ablation electrode 4 is connected with an energy source 24 via an electrical connection 23 for providing electrical energy at the location 5. Preferentially, the energy source 24, the electrical connection 23 and the ablation electrode 4 are adapted to apply radio frequency (RF) energy to the heart 3 at the location 5. The electrical connection 23 is preferentially a wire.

The image providing unit 2 is preferentially adapted to provide an electroanatomic map of the heart 3. In this embodiment, the image providing unit 2 is a storing unit in which the electroanatomic map is stored. The electroanatomic map can be generated by generating a three-dimensional image of the heart 3, for example, by using a computed tomography system, a magnetic resonance imaging system, a nuclear imaging system or an ultrasound imaging system or by impedance, magnetic or electromagnetic-based tracking of the position of the catheter tip, and by measuring the electrical property of the heart at different locations on a wall of the heart, wherein the measured electrical properties are visualized at the respective locations in the three-dimensional image of the heart.

For example, the electroanatomic map can be an activation map reflecting the activation sequence of the anatomical substrate. From this activation map conduction patterns can be derived revealing, for example, zones of late activation or reentrant waves. The information from the activation map can be used to identify ablation targets to which energy should be applied.

The energy application apparatus 1 further comprises a localization unit 6, 7 for localizing the ablation electrode 4 at the location 5. The localization unit comprises an X-ray fluoroscopy system 6 with an X-ray source 25 and an X-ray detector 26. The X-ray source 25 emits an X-ray beam 27 which traverses the heart 3 including the catheter tip 22. The X-ray beam, which has traversed the heart 3, is detected by the X-ray detector 26. The X-ray detector 26 generates electrical signals depending on the detected X-ray beam and the electrical signals are used by a fluoroscopy control unit 28 for generating an X-ray projection image. The fluoroscopy control unit 28 is also adapted to control the X-ray source 25 and the X-ray detector 26. The X-ray source 25 and the X-ray detector 26 can be adapted to be rotatable around the patient 20 for allowing the X-ray fluoroscopy system 6 to generate X-ray projection images in different directions. The X-ray fluoroscopy system is, for example, a computed tomography fluoroscopy system or a C-arm fluoroscopy system. The X-ray projection images are provided to a position determination unit 7 for determining the position of the ablation electrode 4 within the heart 3. For determining the position of the ablation electrode 4 within the heart 3 based on the provided X-ray projection images known position determining methods can be used. For example, the ablation electrode can be recognized in the different X-ray projection images, which allows the position determination unit to determine the paths of the X-rays which have caused the respective projection of the ablation electrode 4. The position determination unit 7 can be adapted to determine the position of the ablation electrode 4 within the heart 3 from the intersection of these paths. Or, an image of the ablation electrode 4 within the heart 3 can be generated from the X-ray projection images, for example, by using a backprojection algorithm, wherein the position determination unit 7 can be adapted to determine the position of the ablation electrode 4 within the heart 3 by recognizing the ablation electrode within the heart 3 in the generated image. The position determination unit 7 can also be adapted to determine the orientation of the catheter, in particular, of the ablation electrode 4.

In other embodiments, the localization unit can comprise a magnetic resonance imaging system for determining the position and preferentially also the orientation of the ablation electrode 4 within the heart 3. The catheter tip 22 can comprise elements for facilitating the determination of the position and preferentially the orientation of the catheter tip 4 by using an imaging system like the X-ray fluoroscopy system 6 or a magnetic resonance imaging system. For example, the catheter tip can comprise a tracking coil, if the catheter tip is used within a magnetic resonance imaging system, or elements that can be identified on an X-ray projection image and that are shaped such that a determination of the position and preferentially orientation of the catheter tip is facilitated by using the X-ray fluoroscopy system 6. The catheter tip can also comprise a location sensor for determining the position and preferentially orientation of the catheter tip within the heart 3. The localisation unit can also be adapted to use electro-magnetic tracking, impedance localization, fiber bragg-based optical shape sensing, or ultrasound localization for localizing the ablation electrode 4 at the location 5. The localization unit is preferentially adapted to allow localizing the catheter tip 22 in realtime.

The catheter tip 22 comprises a sensing unit 18 for generating a sensing signal being indicative of a property of the heart 3 at the location 5, wherein a quality value determining unit 8 is adapted to determine a quality value, which is a depth value in this embodiment, depending on the generated sensing signal. The depth value is indicative of the depth to which the applied energy has altered the heart 3 at the location 5. The sensing unit 18 is an ultrasound unit. In another embodiment, another kind of sensing unit can be used for generating the sensing signal, for example, a magnetic resonance unit, an electrical unit or an optical unit. The quality value determining unit 8 is adapted to determine the depth of a lesion created by applying the energy at the location 5 to the heart 3. In particular, the quality value determining unit 8 is adapted to determine the ablation depth at the location 5. Also the determination of the depth value, in particular, of the ablation depth, can preferentially be performed in realtime.

The determination of an ablation depth from an ultrasound signal provided by the sensing unit 18 is in the following exemplarily described.

Figure 3:
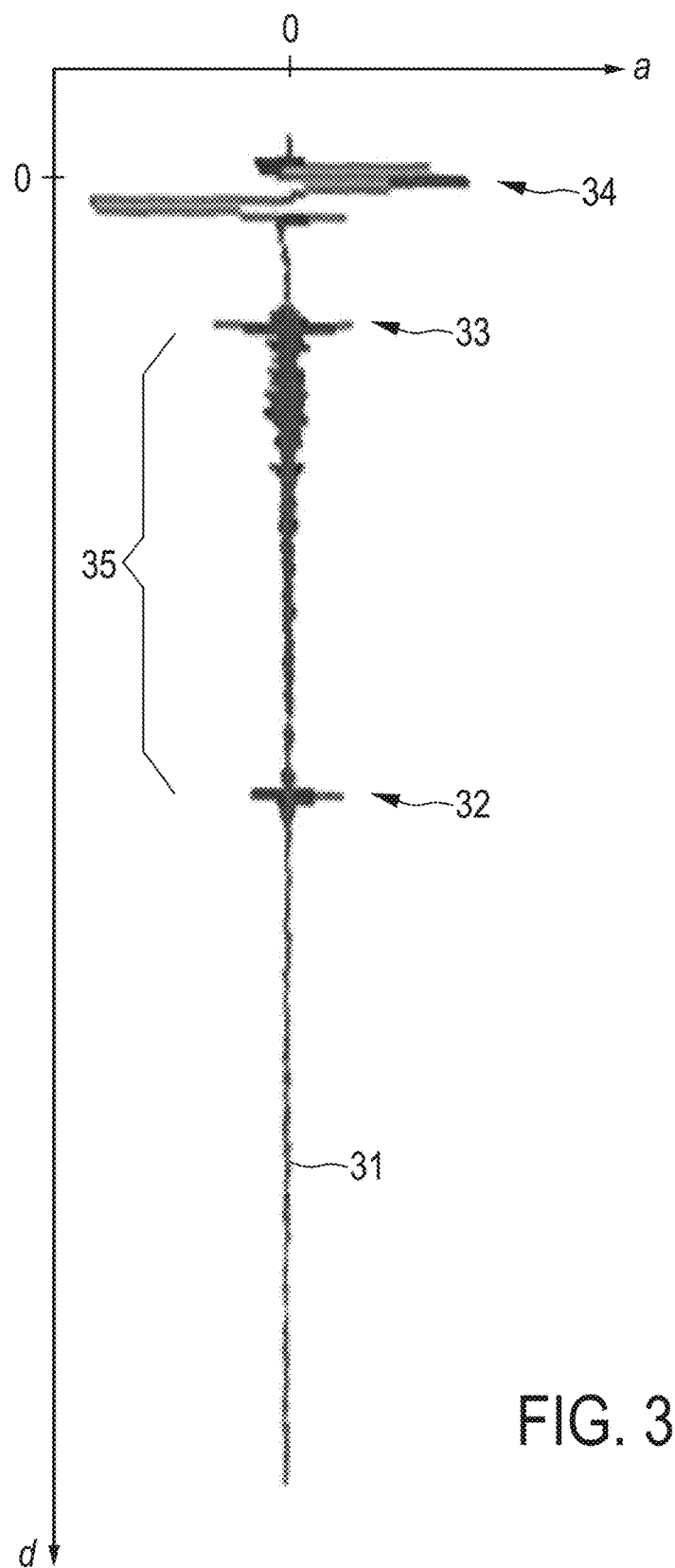
FIG. 3 shows schematically and exemplarily a representation of an echo series produced by reflections of an ultrasound pulse at heart wall tissue.

If an ultrasound pulse is sent out to the object, the ultrasound pulse is reflected at different depths such that echo signals are received by the ultrasound unit 18. The echo signals, which are generated by reflection of the ultrasound pulse at different depths within the object, form an echo series. An echo series 31 is schematically and exemplarily shown in FIG. 3. By considering the speed of sound and the time, at which an echo is recorded after the ultrasound pulse has been sent out to the object, the echo series can be translated into a dependence of an ultrasound reflection property of the object on the depths within the object. In FIG. 3, the amplitude a of the echo series in arbitrary units, which corresponds to the ultrasound reflection property, is shown depending on the depth d in arbitrary units that corresponds to the time, at which the respective echo has been received after the pulse has been sent out into the object.

In this embodiment, the object is a wall of a heart, wherein the ultrasound pulse is sent out into the heart tissue of the wall. In FIG. 3, the regions of the echo series 31 denoted by 33 and 32, correspond to front and back surfaces of the heart wall. The region 34 is directly generated by the electrical pulse sent to the ultrasound transducer. Thus, in a strict sense, the echo series is the graph shown in FIG. 3 without region 34.

The echo series 31 shown in FIG. 3 allows determining the position of the front and back surfaces 33, 32 with respect to the position of the ultrasound unit 18 that emits the ultrasound pulse and receives the echoes. The first measured amplitude in the region 34 marks the position of the ultrasound unit 18. Region 34 is followed by a region comprising an amplitude being substantially zero, in particular, due to homogenous matter like saline solution that mediates the contact between the ultrasound transducer and the tissue surface (coupling medium), and after a while the amplitude increases again in region 33 marking the first reflection at the object, i.e. marking the front surface of the object. A region 35 comprising smaller amplitudes that correspond to reflections/scattering within the heart tissue follows, and then in the region 32 the amplitude increases again significantly thereby marking the back surface of the heart wall. Thus, the echo series 31 allows determining the positions of the front and back surfaces and, thus, the thickness of the wall based on the regions 32 and 33. The region 35 in between is used for determining the ablation depth as will be explained further below.

The quality value determining unit 8 is preferentially adapted to determine the position of the increasing amplitude in region 33 after a region comprising an amplitude value being substantially zero as the position of the front surface of the object. Then, the amplitude substantially decreases in region 35 and the position of the next significant increase of the amplitude (region 32) is determined as the position of the back surface of the heart wall. In other words, after the ring down of the transducer of the ultrasound unit in region 34 a "quiet period" ensues. This quiet period is subsequently terminated by a reflection in region 33 that is associated to the front surface. After this reflection in the region 33 a period 35 occurs that is marked by fast and small changes in the ultrasound intensity. In particular, the envelope of the signal in the period 35 tends to have an exponential decrease in intensity. At the end of the period 35 again a strong reflection is observed in the region 32 that is associated to the back surface. Threshold values can be predefined, in particular relative threshold values can be predefined, wherein the front surface is detected, if a reflection after the "quiet period" exceeds the respective predefined threshold and wherein the back surface is detected, if at the end of period 35 the signal exceeds the respective threshold. The thresholds can be predefined by calibration measurements with walls having known front surface and back surface positions.

The echo series 31 exemplarily shown in FIG. 3 has been generated by an ultrasound pulse that was sent out into the object at a certain time. Several of these ultrasound pulses are sent out to the object at different times, thereby generating echo series at different times. These echo series, which are obtained from different ultrasound pulses at different times, and, thus, which belong to different times, form dynamic echo series. The ultrasound signal which depends on the received dynamic echo series represents therefore the ultrasound reflection properties of the object at different depths and at different times. Such an ultrasound signal is schematically and exemplarily shown in FIG. 4.

Figure 4:
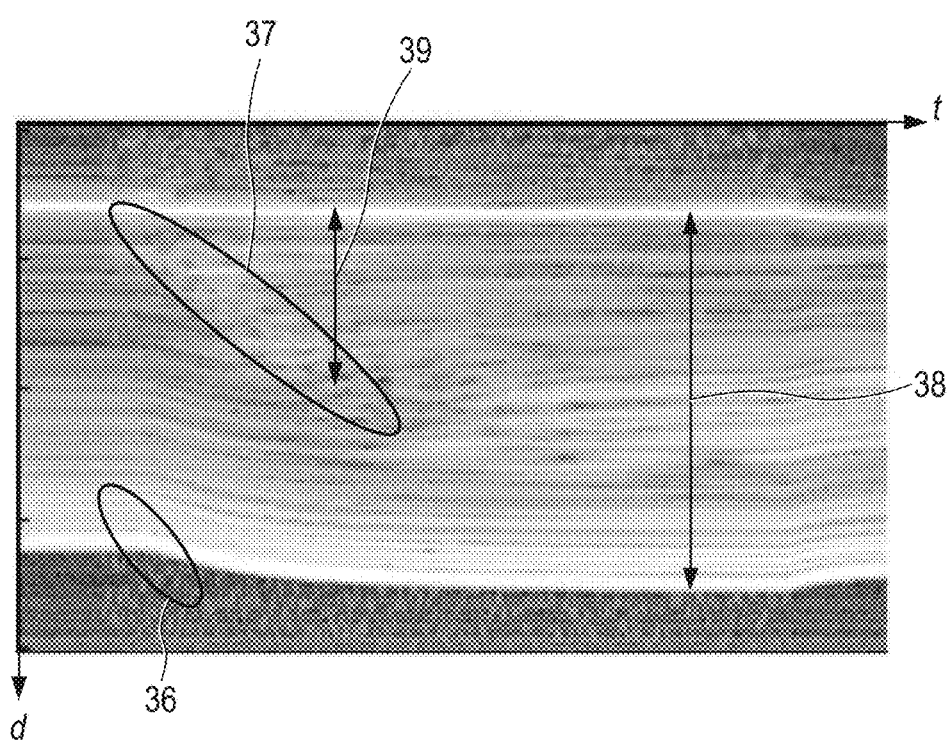
FIG. 4 shows schematically and exemplarily a two-dimensional representation of an ultrasound signal that depends on dynamic echo series.

In FIG. 4, different amplitudes of the ultrasound signal are indicated by different brightness, wherein a higher brightness corresponds to a larger amplitude. The amplitude is shown depending on the depth d and the time t at which the respective echo series has been generated. The ultrasound signal shown in FIG. 4 forms an image that can be regarded as M-mode image.

By performing an ablation procedure, a lesion is generated in the heart wall, wherein the ablation depth is defined by the boundary of the lesion within the heart wall tissue.

The quality value determining unit 8 is adapted to determine discontinuities in the ultrasound signal and to determine the ablation depth as a depth of the ultrasound signal at which the discontinuities occur. For example, in FIG. 4 in the first ellipse 36 only continuous variations of the ultrasound signal are present indicating a macroscopic tissue expansion of the heart wall tissue during applying ablation energy to the tissue. In the second ellipse 37 discontinuities in the variation of the ultrasound signal can be observed that indicate the ablation depth. Thus, FIG. 4 shows the progression of the lesion, i.e. the increasing ablation depth, in the second ellipse 37. Based on the observed discontinuities the ablation depth is determined as indicated exemplarily for a certain time by the second double arrow 39, whereas the first double arrow 38 indicates the thickness of the heart wall for a certain time. It should be noted that also the thickness of the heart wall changes with time during performing an ablation procedure due to a macroscopic tissue expansion as can be seen in FIG. 4.

For determining the ablation quality the quality value determining unit 8 can be adapted to estimate time-resolved shifts, in particular, macroscopic shifts, in the ultrasound signal due to tissue expansion. In particular, the continuous variations of the ultrasound signal are detected and used for determining the shifts in the ultrasound signal due to tissue expansion for each time for which an ultrasound pulse has been sent out into the object and reflected by the object at different depths. Then, the quality value determining unit 8 calculates a shift-compensated ultrasound signal to correct for the shift caused by tissue expansion during ablation. In particular, for different times the amplitude values shown in, for example, FIG. 4 are moved vertically in correspondence with the determined shift for compensating this shift caused by tissue expansion. Then, preferentially the quality value determining unit 8 suppresses noise in the shift-compensated ultrasound signal using, for example, a Gaussian filter with, for example, $\sigma=25$. In an embodiment, the quality value determining unit 8 is adapted to follow lines corresponding to a constant depth in the shift-compensated ultrasound signal with time, i.e. to follow horizontal lines in a representation of the shift-compensated ultrasound signal that corresponds to the representation shown in FIG. 4, until a disjunctive event occurs. The length of the horizontal lines before this disjunctive event occurs is determined by means of correlation statistics. Then, the quality value determining unit 8 is adapted to assign ablated/non-ablated regions based on the determined lengths of connected stretches with a cut-off parameter that remains flexible. The cut-off parameter is, for example, 0.25 s. In particular, in a shift-compensated ultrasound image temporally adjacent pixels on a horizontal line are compared. If along a horizontal line a lesion boundary is not present, the pixels along the horizontal line tend to have roughly the same intensity and only slow variations may occur. In contrast, if a lesion boundary, i.e. the ablation lesion, reaches the horizontal line, the intensity of the pixels in this line change significantly. The depth associated with this significant change in the intensity defines the ablation depth. Preferentially, the quality value determining unit 8 is adapted to determine stretches along a horizontal line comprising pixel values having substantially the same intensity. When an ablation front reaches a certain horizontal line, a significant decrease in the length of the stretches in this horizontal line is observed. If the length of the stretches is below a predefined threshold, the quality value determining unit 8 determines the ablation depth as the depth associated to the location at which the length of the stretches is below this predefined threshold. This predefined threshold can be determined by calibration measurements, wherein ultrasound signals are generated by sending ultrasound pulses into the object having a known ablation depth. Also the similarity measure for determining whether adjacent pixel intensity values on a horizontal line are similar or not, i.e. whether two adjacent pixel value intensities on a horizontal line belong to the same stretch, can be determined by this calibration. For example, by calibration a relative threshold can be defined indicating the maximum relative difference in the pixel value intensities leading to the decision that these pixel value intensity values are regarded as being similar, i.e. two pixel value intensities are regarded as being similar if their relative difference is equal to or smaller than the maximum relative difference that is preferentially determined by calibration. In an embodiment, stretches having a length larger than 0.25 s, further preferred larger than 0.5 s and even further preferred larger than 1 s, are regarded as indicating that the ablation has not yet occurred at the depth corresponding to the respective horizontal line.

The energy application apparatus 1 further comprises a navigation unit 29 for allowing the catheter 21, in particular, the catheter tip 22, to be navigated to a desired location within the object 3. The navigation unit 29 can be adapted to allow a user to navigate the catheter 21 completely by hand or semi-automatically depending on a determined position and preferentially orientation of the catheter tip 22. The catheter 22 comprises build-in guiding means (not shown in FIG. 1), which can be controlled by the navigation unit 29. The catheter 29 can, for example, be steered and navigated by the use of steering wires in order to guide the catheter tip 22 to a desired location within the object 3.

Figure 5:
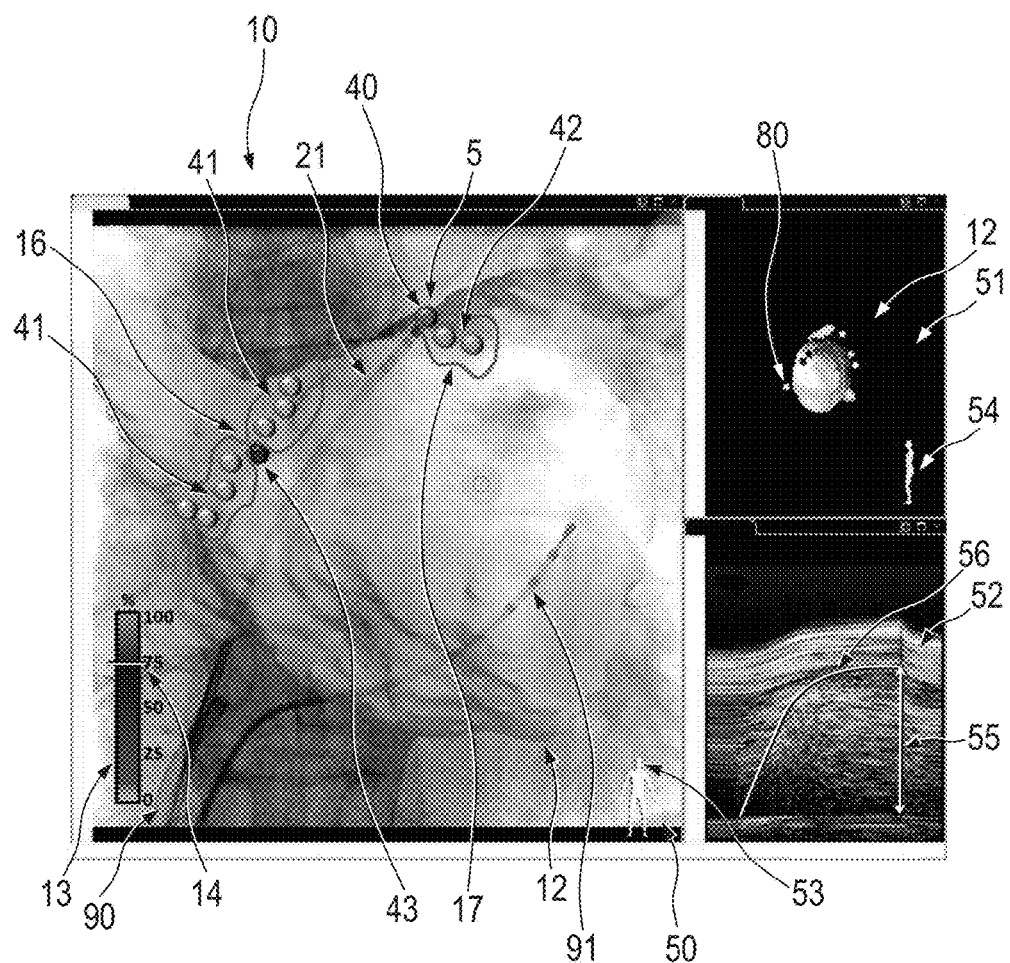
FIG. 5 shows schematically and exemplarily an embodiment of a display.

The energy application apparatus 1 further comprises a visual property assigning unit 9 for assigning a visual property to the location 5 depending on the depth value, in particular, depending on the ablation depth, provided by the quality value determining unit 8. A display 10 displays the provided image, in particular, the electroanatomic map of the heart, and the assigned visual property at the location 5 on the heart shown in the image. The visual property assigning unit 9 is preferentially adapted to assign a color as the visual property depending on the provided depth value, in particular, depending on the ablation depth at the location 5 at which energy is applied. The depth value is preferentially provided with respect to a thickness of a wall of the heart 3. In this embodiment, the ablation depth is provided as a degree of transmurality, wherein the visual property assigning unit 9 is adapted to assign a color depending on the degree of transmurality. FIG. 5 shows schematically and exemplarily the display 10 showing the electroanatomic map 12 of the heart 3. At the location 5 energy is applied to the heart 3 via the ablation electrode. The dot 40 at the location 5 has a color indicating the degree of transmurality at this location. The further dots 41, 42, 43 shown in FIG. 5 mark ablation sites at which energy has already been applied. The color of these dots 41, 42, 43 corresponds to the respective degree of transmurality. Completed lesions, e.g. transmural lesions, are preferentially shown in a first color, for example, in a green color, while a new lesion being created at the tip of the ablation catheter is shown with a color reflecting its instantaneous ablation depth.

The visualization apparatus further comprises a gauge element 13 shown on the display 10, wherein the gauge element 13 is adapted to indicate a relation between a visual property and the depth value. In this embodiment, the gauge element 13 indicates which color belongs to which ablation depth, in particular, to which degree of transmurality. In another embodiment, the gauge element can also be adapted to indicate which color belongs to which absolute ablation depth. The absolute ablation depth can be indicated, for example, in millimeters. The gauge element 13 comprises a marker 14 indicating the depth to which the actually applied energy has altered the heart 3 based on the depth value provided by the quality value determining unit 8. In this embodiment, the marker 14 indicates the actual degree of transmurality at the location 5 at which energy is currently applied, wherein the marker 14 is a black line which moves in accordance with the changing degree of transmurality at the location 5.

The depth value is preferentially repeatedly provided during applying energy to the heart 3, wherein the visual property assigning unit 9 is adapted to repeatedly assign a visual property to the location 5 depending on the respective actually provided depth value and wherein the display 10 is adapted to repeatedly display the provided image and the respective actually assigned visual property at the location 5 on the heart 3 shown in the image. This allows indicating the respective depth to which the applied energy has influenced the heart 3 in realtime while applying energy at the location 5. In particular, the marker 14 on the gauge element 13 moves up the gauge element scale in realtime as the ablation depth increases, wherein the position of the marker on the gauge element 13 indicates the instantaneous ablation depth. Also the color of the dot 40 at the location 5 changes with increasing ablation depth, i.e. with increasing degree of transmurality, in realtime in accordance with the relation between the color and the degree of transmurality shown by the gauge element 13. An incomplete transmural lesion which corresponds to a degree of transmurality smaller than 100 percent is clearly recognizable for the person who applies energy to the heart 3 by the color provided at the respective ablation site. For example, the dot indicated in FIG. 5 by reference number 43 can comprise a red color indicating a low degree of transmurality, for example, a degree of transmurality of about 30 percent.

Also treatment planning can be performed by using the display 10, wherein desired ablation sites can be placed on the electroanatomic map of the heart as dots having a color indicting that at these desired ablation sites energy has to be applied. The color of these dots corresponds preferentially to a small degree of transmurality, in particular, to a degree of transmurality being zero, thereby indicating that energy has still to be delivered at these sites.

The energy application apparatus further comprises a transmural region calculation unit 15 for calculating a transmural region of the heart 3 based on the provided depth value. The display 10 is adapted to show the calculated transmural region on the image 12 of the heart 3. In this embodiment, depth values, i.e. ablation depths, are provided for several locations, wherein these depth values and the locations are used for calculating transmural regions, which are indicated by the lines 16, 17 surrounding the respective transmural region on the heart 3. The transmural region calculation unit 15 is preferentially adapted to also use prior art on lesion formation dynamics for calculating one or several transmural regions. The transmural regions show areas were complete and transmural lesions have been formed. In this way, a person can directly target locations in which a gap in the lesion line occurs. In particular, the lines 16, 17 indicate suitable ablation sites based on the requirement that they form continuous ablation fronts with the already present ablations. As can be seen in FIG. 5, the lines 16 touch each other, thereby indicating that there is a current leakage path at this touch location, which will need to be addressed.

The display 10 comprises three regions. A first region 50 shows a frontal view as indicated by the person 53. A second region 51 shows the heart in a side view as indicated by the person 54 and a third region 52 shows an ultrasound image showing the tissue at the location 5. The ultrasound image shown in the third region 52 corresponds to the ultrasound image described above with reference to FIG. 4. In the third region 52 the line 56 indicates the lesion development with time and the line and arrows 55 indicate the actual ablation depth.

The white dots 80 shown in the second region 51 can be used for registering the electroanatomical map to a realtime fluoroscopy image. However, the second region 51 can also be adapted to not show these white dots. The first region 50 shows the catheter 21 and further elements 90, 91 present in the heart 3. In other embodiments, the further elements 90, 91 may not be present in the first region.

Although a certain configuration of the catheter tip 21 has been described above with reference to FIG. 2, the catheter tip 21 can also have another configuration. Preferred configurations of the catheter tip 21 will in the following be described with reference to FIGS. 6 to 11*b*.

Figure 6:
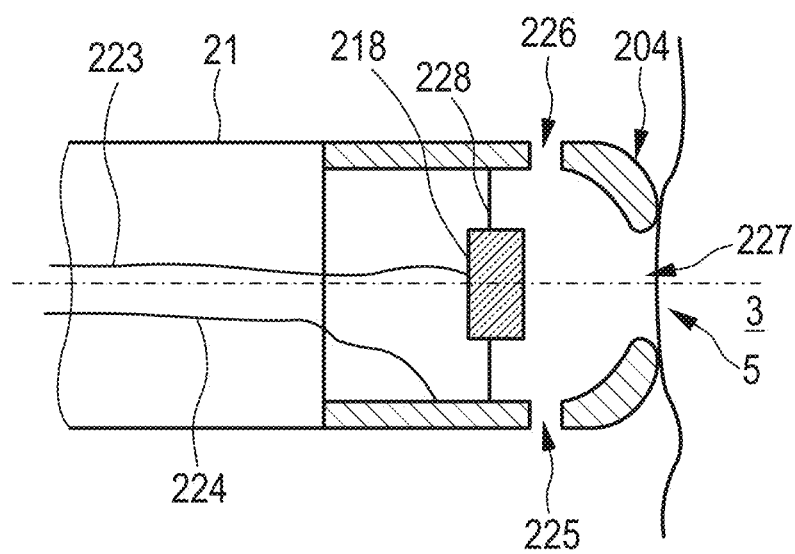
FIGS. 6 to 11*b* show several embodiments of a catheter tip.

The catheter tip 21 shown in FIG. 6 comprises an energy application element 204 being an solid tip ablation electrode with a plurality of openings. The ablation electrode 204 comprises irrigation holes 225, 226 and 227 and is electrically connected via a wire 224. A sensing unit 218 being an ultrasound transducer is located within the ablation electrode 204 for generating an ultrasound signal being indicative of ultrasound properties of the tissue 3 at the location 5. The ultrasound transducer 218 is held within the ablation electrode 204 via holding elements 228. The ultrasound transducer 218 can be connected to the quality value determining unit 8 via a wire 223.

Figure 7A:
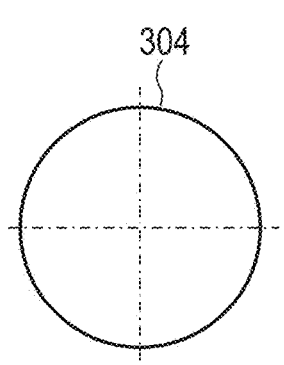
Figure 7B:
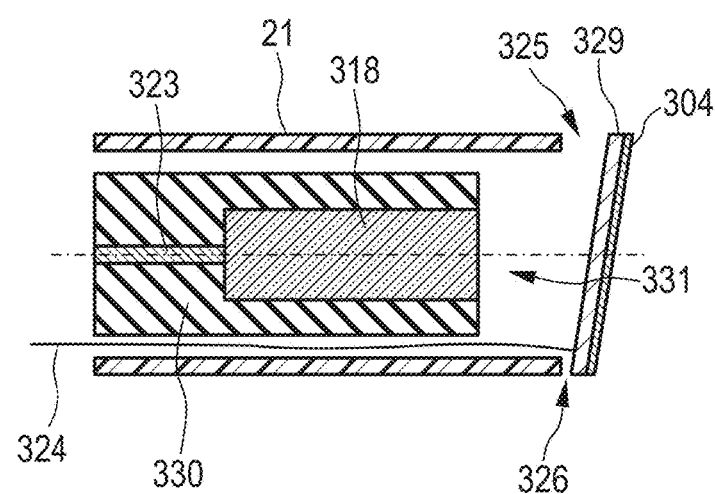

FIGS. 7*a* and 7*b* show schematically and exemplarily a further embodiment of the catheter tip 21. FIG. 7*a* shows a front view and FIG. 7*b* shows a cross-sectional side view of the catheter tip. In this embodiment the catheter tip 21 comprises an ablation electrode 304 being preferentially a platinum layer or a layer of another metal on a TPX window 329. The ablation electrode 304 is electrically connected via the wire 324. The catheter tip 21 comprises a lumen 331 for irrigation and irrigation openings 325, 326. The TPX window, which is an acoustical transparent window, is tilted with respect to the front face of an ultrasound transducer 318 which is located within the catheter tip 21, in order to minimize specular reflection and to avoid secondary reflections (reverberations). The tilted angle is, for example, 10 degrees, in order to avoid the above mentioned problems. TPX (polymethylpentene) is a plastic and is almost completely transparent to ultrasound. The ultrasound transducer 318 being a sensing unit for generating a sensing signal being indicative of a property of the object is located within a casing 330 within the catheter 21 and is connected to the quality value determining unit 8 via a wire 323.

Figure 8A:
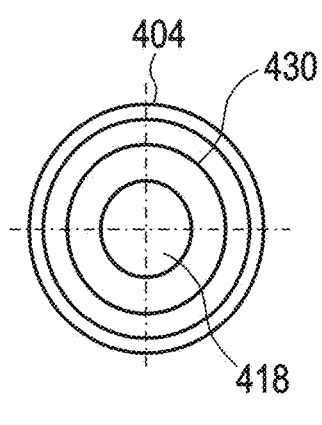
Figure 8B:
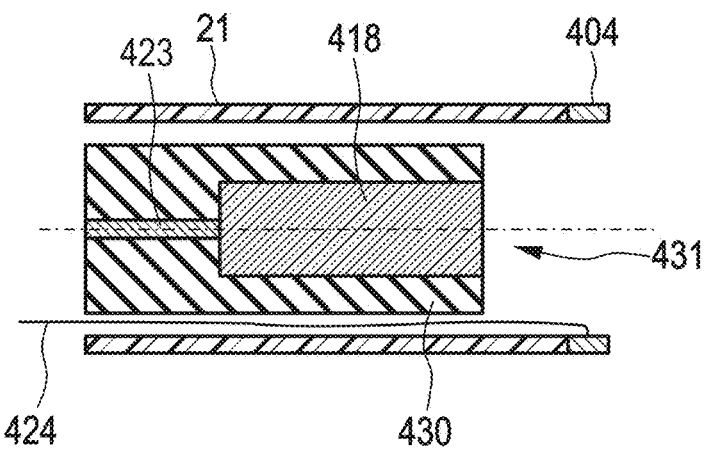

FIGS. 8*a* and 8*b* show schematically and exemplarily a further embodiment of the catheter tip 21. FIG. 8*a* shows a front view and FIG. 8*b* shows a cross-sectional side view of the catheter tip. The catheter tip comprises an ablation ring electrode 404 made of platinum or another metal. The ablation ring electrode 404 is electrically connected via the wire 424. An ultrasound transducer 418 is located within the catheter tip 21 and connected to the quality value determining unit 8 via the wire 423. In particular, the ultrasound transducer 418 is located within a casing 430 which is located within the catheter tip 21. The catheter 21 further comprises an irrigation lumen 431 for irrigation purposes, wherein irrigation fluid can leave the catheter tip 21 through the ablation ring electrode 404. The ablation ring electrode 404 does not radially protrude from the inner side of the outer wall of the catheter tip 21.

Figure 9A:
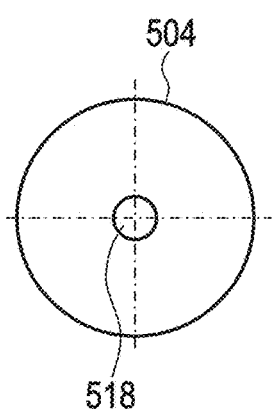
Figure 9B:
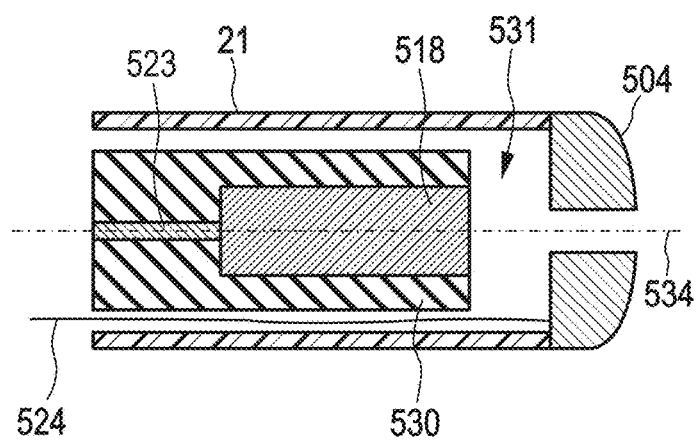

FIGS. 9*a* and 9*b* show schematically and exemplarily a further embodiment of the catheter tip 21. FIG. 9*a* shows a front view and FIG. 9*b* shows a cross-sectional side view of the catheter tip. The catheter tip 21 comprises an ablation electrode 504 located at the distal ends of an outer wall of the catheter tip 21. The ablation electrode 504 protrudes towards the direction of the longitudinal axis 534 of the catheter tip 21. Ultrasound waves from the ultrasound transducer 518, which is located within the catheter tip 21, are therefore partially reflected by the ablation ring electrode 504 in order to have a reference of where the ablation tip is situated with respect to the tissue. Upon bringing the catheter towards the tissue, the ultrasound signal from the front wall of the tissue will move towards the reference point of the ultrasound signal showing the place of the catheter tip (FIG. 15) The ablation ring electrode 504 is preferentially made of platinum, but can also be made of another metal. The ultrasound transducer 518 is located within a casing 530 within the catheter tip 21 and connected to the quality value determining unit 8 via a wire 523. The ablation electrode 504 is electrically connected via the wire 524. The catheter 21 further comprises an irrigation lumen 531, wherein irrigation fluid can leave the catheter 21 through the ablation ring electrode 504.

Figure 10A:
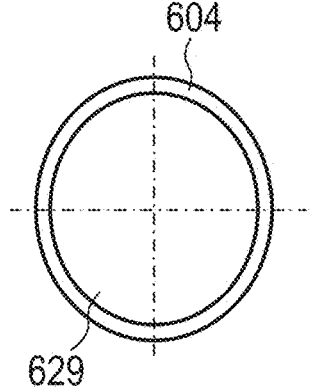
Figure 10B:
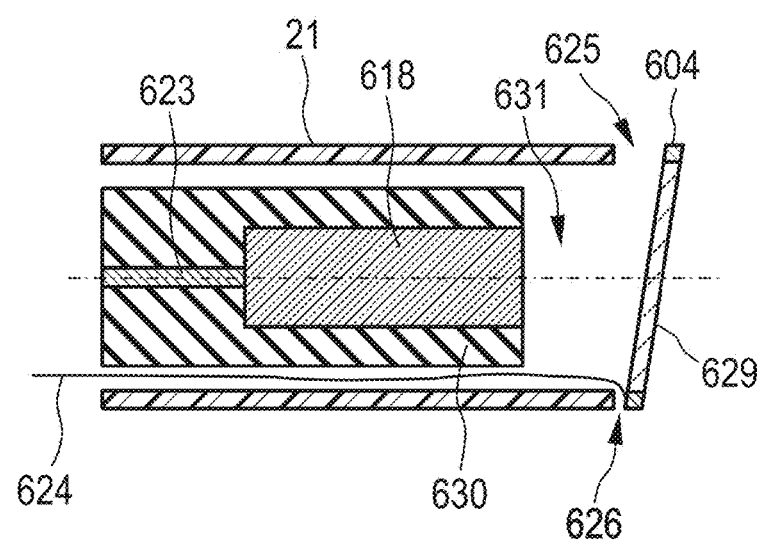

A further embodiment of the catheter tip 21 is schematically and exemplarily shown in FIGS. 10*b* and 10*b*. FIG. 10*a* shows a front view and FIG. 10*b* shows a cross-sectional side view of the catheter tip. The catheter tip 21 comprises an ablation ring electrode 604, which surrounds an acoustically transparent foil 629 which is preferentially a TPX foil. Ultrasound waves generated by an ultrasound transducer located within the catheter tip 21 are partially reflected by the foil 629. The ablation ring electrode 604 is made of platinum or another metal and electrically connected via a wire 624. The ultrasound transducer 618 is located within a casing 630 and connected to the quality value determining unit 8 via a wire 623. The plane containing the ring electrode 604 and the foil 629 is preferentially tilted with respect to the front face of the ultrasound transducer 618. The catheter 21 further comprises an irrigation lumen 631, wherein irrigation fluid can leave the catheter 21 via irrigation openings 625, 626.

The casings, which have been described above with reference to FIGS. 7*a* to 10*b*, are preferentially used for holding the ultrasound transducer and for mounting the ultrasound transducer within the catheter tip. Preferentially, around the casing irrigation fluid is brought forward via one or multiple channels.

Robotic navigation can be used in ablation procedures to remotely steer the catheter to the target tissue. The described catheter tips can be adapted such that they can be controlled by external magnets. This typically requires the incorporation of small coils in the catheter tip. The catheter tips can also be adapted to be remotely steered by mechanical navigation by using, for example, pull wires. A catheter sheath can be used in which the respective catheter can be introduced. Navigation of the sheath can be tightly controlled resulting in a stable fixation of the catheter.

In combination with cardiac motion, assessment of tissue contact is generally very crucial in such a configuration. Upon integration of at least one ultrasound element in the tip of the catheter sheath, the contact between the catheter tip and the tissue can be assessed. In this configuration, the localization of the sheath with respect to the catheter is fixed, whereas the cardiac motion can cause the tissue to move away from the transducer in case of poor contact. In case of good contact, the distance between the ultrasound element and the tissue remains constant.

Figure 11A:
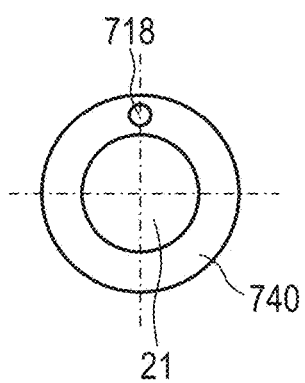
Figure 11B:
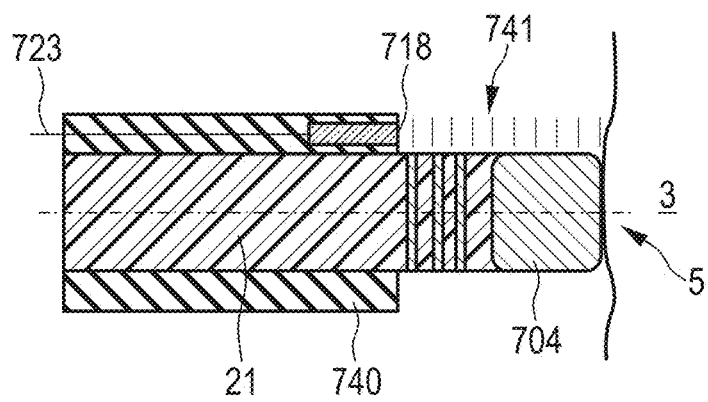

An embodiment with an ultrasound transducer integrated in a catheter sheath is schematically and exemplarily shown in FIGS. 11*a* and 11*b*. FIG. 11*a* shows a front view and FIG. 11*b* shows a cross-sectional side view of the catheter tip 21 with the catheter sheath 740. An ultrasound transducer 718 is located in the wall of the catheter sheath 740 such that ultrasound waves 741 can be sent from the distal end of the catheter sheath to the tissue 3. The ultrasound transducer 718 is connected with the quality value determining unit 8 via the wire 723. The catheter tip 21 comprises an ablation electrode 704 for applying ablation energy to the tissue 3 at the location 5. The sheath can also be provided with a connection for irrigation, to flush the blood in front of the ultrasound transducer.

Instead of using the wires described above with reference to FIGS. 6 to 11b, other electrical connections can be used.

The above described catheter tips are adapted for forward-looking imaging. However, they can also be adapted to be used in combination with multi-directional imaging. Moreover, the described catheter tips can also be extended with sensors for measuring physiological parameters such as temperature, impedance, electrograms, et cetera, and instead of using single-element transducers for ultrasound imaging, MUT-based ultrasound sensors, i.e. micro-machined ultrasound transducers, can be used.

During a cardiac cycle it is preferred that the energy application element remains in constant contact with the tissue. But, this is often not the case due to cardiac motion. The lesion size largely depends on contact force that is applied. But, this is subjective to large variations depending, for example, on the anatomical site of ablation and the physician performing the procedure. Feedback about the contact can be used by the physician to decide on whether to start ablation at a specific spot or to continue to maneuver the catheter tip. In addition, this feedback can be used to adjust the ablation settings like RF power, ablation time, irrigation flow rate, et cetera.

The quality value determining unit 8 can therefore also be adapted to determine a contact value as quality value, wherein the contact value is indicative of a degree of contact between the energy application element and the object, in particular, the tissue to which energy has to be applied. The quality value determining unit is adapted to determine the contact value depending on the ultrasound signal received from the ultrasound unit located at the catheter tip. As already mentioned above, the catheter tip comprises preferentially a window that is substantially transparent to ultrasound or an opening like an irrigation hole through which ultrasound waves are sent and received. The received ultrasound waves are transformed into an electrical ultrasound signal which is provided to the quality value determining unit 8 for determining the contact value. In particular, the quality value determining unit 8 is preferentially adapted to identify the boundary of the catheter tip on the acoustical path and to localize the front wall of the object, i.e. in this embodiment of the tissue, with respect to the boundary of the catheter tip on the acoustical path. The contact value can then be determined based on the localization of the front wall of the object with respect to the boundary of the catheter tip on the acoustical path.

As already described above with reference to FIG. 3, the positions of the boundary of the catheter tip and of the front wall of the tissue can be determined from the echo series 31 received by the respective ultrasound transducer. In FIG. 3, the region of the amplitude 34 marks the position of the boundary of the catheter tip and the region of the amplitude 33 marks the position of the front wall of the tissue on the acoustical path. The quality value determining unit 8 can therefore be adapted to determine the distance between the regions, which are denoted by reference numbers 34 and 33 in FIG. 3, for example, by determining a position at which the echo series 31 firstly exceeds a threshold and by determining the position at which the echo series 31 exceeds a threshold after a quiet phase between the positions 34 and 33. The thresholds can be determined by calibration, wherein the positions of the boundary of the catheter tip and of the front wall of the tissue are known. The contact value preferentially depends on the distance between the determined boundary of the catheter tip and the determined position of the front wall of the tissue. In particular, the quality value is proportional to this distance. Alternatively, if the catheter tip comprises a TPX window, the deformation of the TPX window can be used for determining the contact value, which is expected to be larger with stronger contact. The deformation can be calculated from the acoustical path length between the ultrasound transducer and the TPX window. Since the TPX window is partly transparent to the ultrasound waves, also the TPX window is visible in the received echo series. Therefore, the distance between the TPX window and the ultrasound transducer can be determined from the echo series and a contact value can be determined which is, for example, proportional to this distance. If instead of the TPX window another window is used, which is partly transparent to the ultrasound waves, the contact value can be determined similarly based on the deformation of this window.

If the catheter tip described above with reference to FIGS. 7a and 7b is used, the reflection from the TPX window, which is visible in the received echo series, is preferentially used for determining the contact value. This reflection can be used for determining the distance between the boundary of the catheter tip defined by this reflection and the front wall of the tissue or for determining the distance between the TPX window and the ultrasound transducer, wherein it is assumed that depending on the degree of contact between the tissue and the catheter tip the TPX window is deformed, thereby modifying the distance between the ultrasound transducer and the TPX window.

If the catheter tip described above with reference to FIG. 8a and FIG. 8b is used, the outer boundary of the catheter tip defined by the ablation ring electrode format 404 is preferentially calculated from the distance between the ultrasound transducer 418 and the outer boundary of the catheter tip defined by the ablation ring electrode 404 considering the speed of sound in the irrigation fluid at the relevant temperature, for example, in water at 20° C., or it is determined in advance in a test measurement, where the catheter tip is brought in contact with a hard ultrasound reflector. Also in this embodiment, the contact values are preferentially determined depending on the distance between the outer boundary of the catheter tip and the front wall of the tissue.

If the embodiment of the catheter tip described above with reference to FIGS. 9a and 9b is used, the position of the outer boundary of the catheter tip defined by the position of the ablation ring electrode 504 along the acoustic path is preferentially detected by detecting the partial reflection of the ultrasound waves by the ablation ring electrode 504, which protrudes into the acoustical path.

The visual property assigning unit is preferentially adapted to assign a visual property to the location 5 also depending on the contact value. Preferentially, a color is assigned to the location depending on the depth value and an intensity is assigned to the location depending on the contact value. The provided image 12 and the assigned visual properties can be displayed at the location 5 on the object shown in the image 12 by using the display 10 described above with reference to FIG. 5. However, instead of using this display 10, another embodiment of a display can be used for displaying the provided image and the assigned visual properties like the display 810 described in the following with reference to FIGS. 12 to 16.

The display 810 comprises five regions. A first region 850 showing a frontal view of an electroanatomic map of the heart 3 as indicated by the person 853. A second region 851 shows the electroanatomic map in a side view as indicated by the person 854. A third region 861 indicates whether the ablation energy ("RF") is on or off and whether the catheter tip is in steady contact with the tissue or not. A fourth region 860 is provided for showing an M-mode image indicating a quality of contact and the fifth region 852 is provided for showing an ultrasound image of the tissue, which corresponds to the ultrasound image described above with reference to FIG. 4.

Figure 12:
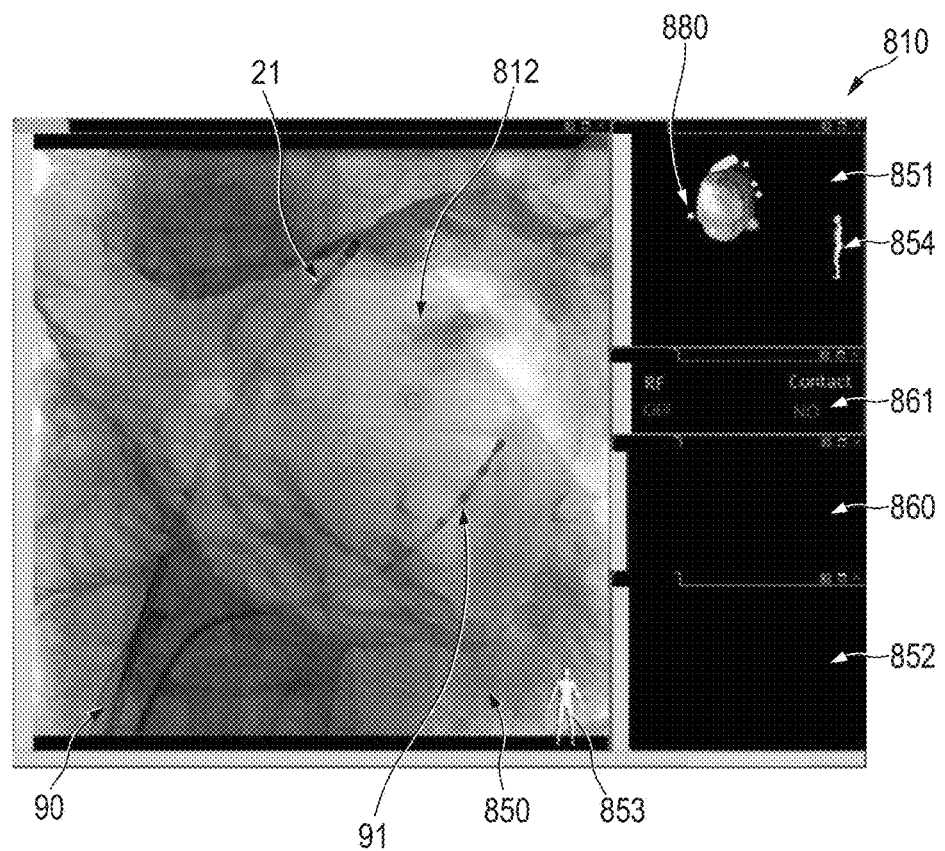
FIG. 12 shows schematically an embodiment of a display at the beginning of a workflow for applying energy.
Figure 13:
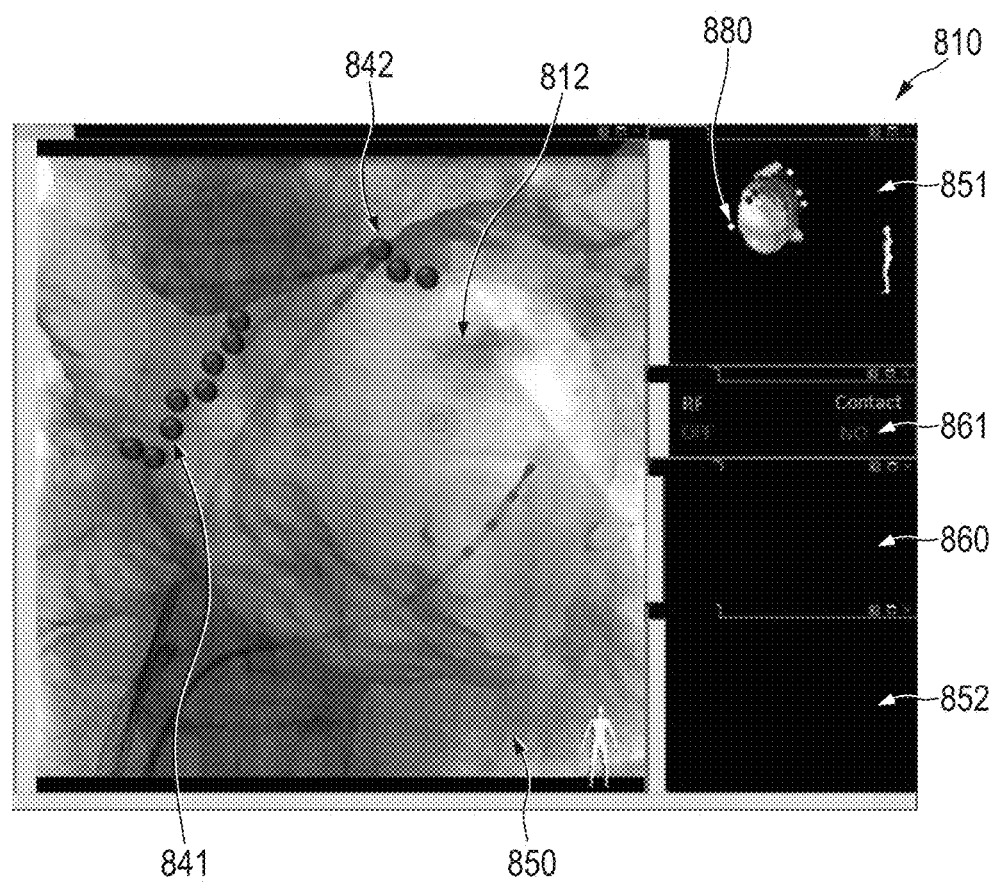
FIG. 13 shows schematically an embodiment of a display with marked locations where energy should be applied.

FIG. 12 shows the display 801 in the beginning of a workflow for applying ablation energy to the heart 3. For planning an ablation treatment, a user can mark locations on the electroanamotic map 812 with dots 841, 842, at which ablation energy should be applied, as shown in FIG. 13. An input unit like a keyboard or a mouse can be used for adding the dots 841, 842 to the first region 850.

Figure 14:
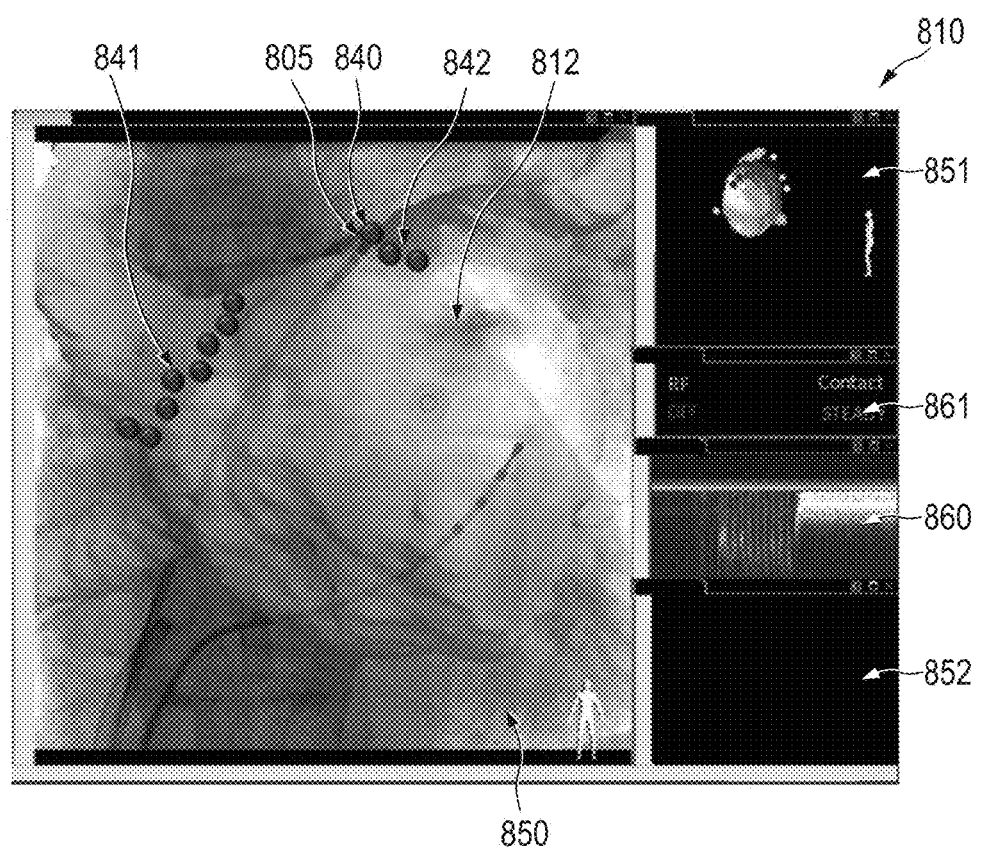
FIG. 14 shows schematically an embodiment of a display indicating the quality of contact between the catheter tip and the tissue to which energy should be applied.

A user can then try to bring the catheter tip 21 in steady contact with the tissue, in particular, with the heart wall. For example, a user can try to contact the location 805 marked by the dot 840, wherein, while trying to contact the tissue, an M-mode image is shown in the fourth region 860 of the display 810 as illustrated in FIG. 14. The M-mode image shown in the fourth region 860 is indicative of the quality of the contact between the catheter tip and the tissue as will be described in the following with reference to FIG. 15.

Figure 15:
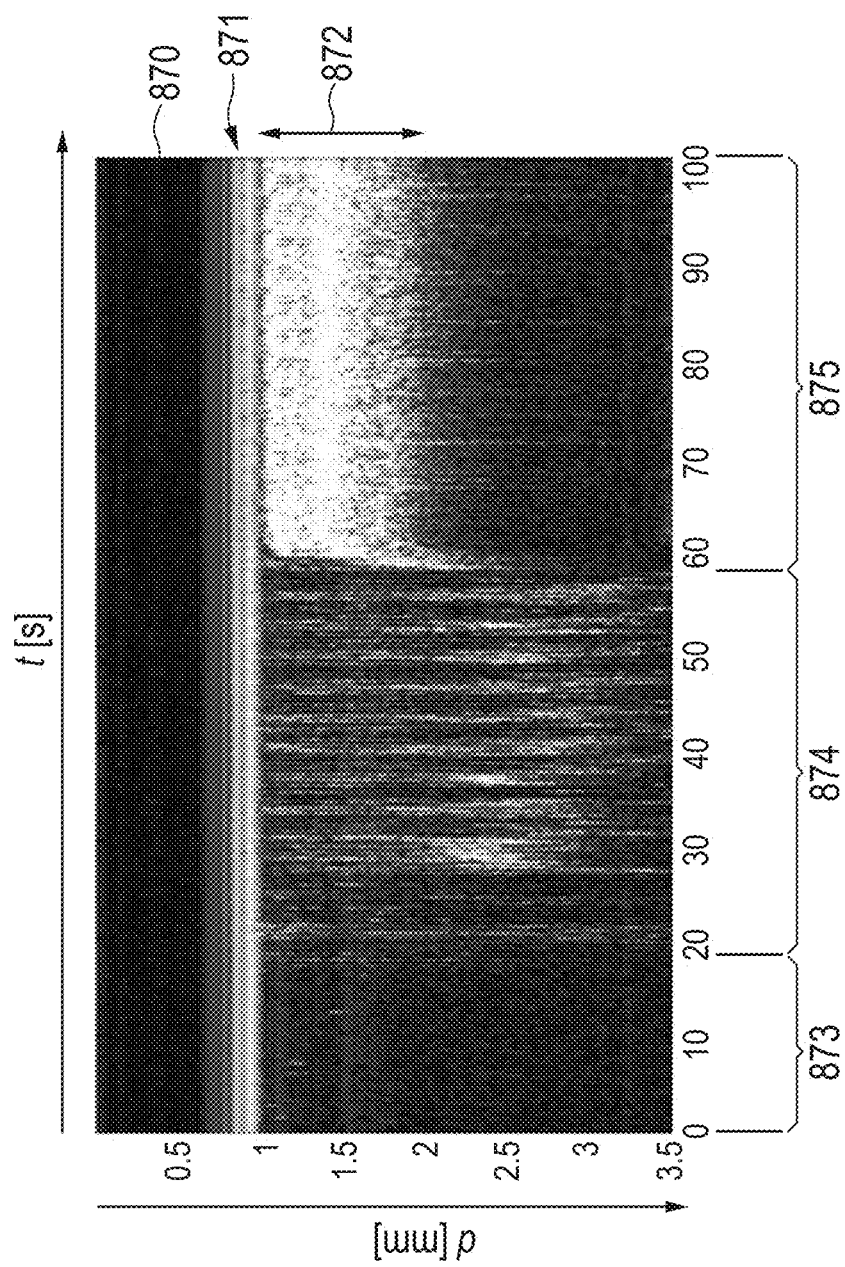
FIG. 15 shows an M-mode image indicating a degree of contact between a catheter tip and the object.
Figure 16:
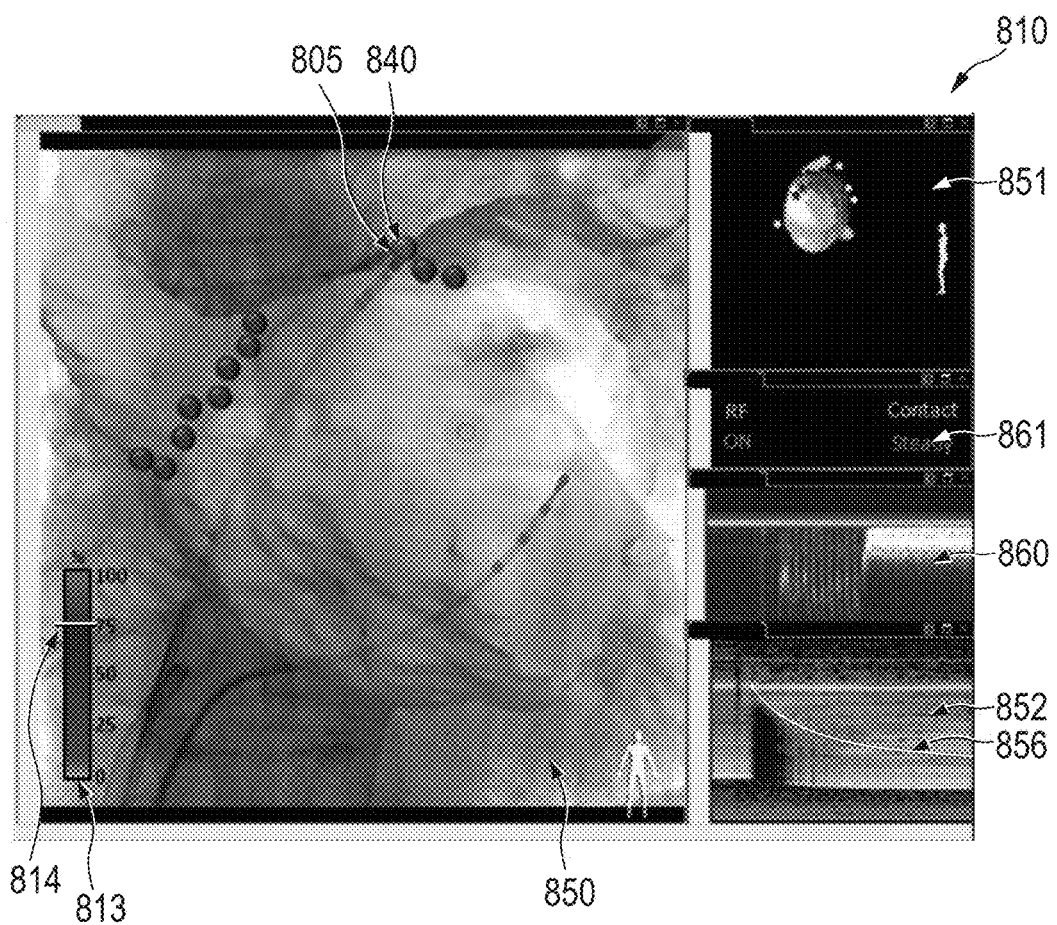
FIG. 16 shows schematically an embodiment of a display indicating an ultrasound image of the tissue to which energy is applied.

FIG. 15 shows exemplarily an M-mode image 870, wherein the time dependence is shown along the horizontal axis in seconds and the depth dependence is shown along the vertical axis in millimeters. The position of the outer boundary of the catheter tip 871 can clearly be identified in the M-mode image 870. In a first region 873 there is no contact between the catheter tip and the tissue, therefore substantially only the catheter tip boundary is visible in this part of the M-mode image. An intermediate region 874 indicates an intermittent or poor contact, because the vertical lines, i.e. the A-lines, in the M-mode image continuously change due to cardiac motion. In a third region 875 the A-lines remain substantially stable and the back wall of the tissue is clearly visible. The tissue thickness can therefore be determined and is indicated in FIG. 15 by the double arrow 872. This third region 875 corresponds to a good steady contact between the catheter tip and the tissue. If a user tries to bring a catheter tip in steady contact with the tissue, the user can look at the fourth region 860 of the display 810, i.e. at the M-mode image 870 shown in the fourth region 860, in order to check, whether the tissue thickness is clearly visible in the M-mode image 870, indicating that a steady contact between the catheter tip and the tissue has been reached. In addition or alternatively, the quality value determining unit 8 can determine the contact value and visualize the dot 840 depending on the determined contact value. For example, the intensity of the dot 840 can be modified depending on the contact value. The quality value determining unit 8 can be adapted to determine the degree of contact as described above, for example, depending on the distance between the position of the outer boundary of the catheter tip and the position of the front wall of the tissue, or depending on the behavior of the ultrasound signal in the M-mode image. In the situation shown in FIG. 15, a steady contact between the catheter tip and the tissue has been reached and this steady contact is indicated in the third region 861 of the display 810.

After the steady contact between the catheter tip and the tissue has been reached, energy is applied to the location 805. In this embodiment, RF ablation energy is applied to the location 805 and in the third region 861 it is indicated that "RF" is "ON".

The ultrasound image, which corresponds to the ultrasound image described above with reference to FIG. 4, is shown in the fifth region 852, wherein a line 856 indicates the ablation depth. The quality value determining unit 8 determines the depth value and the dot 840 at the location 805 is colored depending on the determined depth value. Moreover, a gauge element 813 is shown in the first region 850, which is similar to the gauge element 13 described above with reference to FIG. 5. Also in this stage of the workflow, the quality value determining unit 8 can determine the contact value and the intensity of the dot 840 can be modified, if the degree of contact between the catheter tip and the tissue changes. For example, if the catheter tip looses steady contact to the tissue, the intensity of the dot can be increased or decreased. The user can therefore readily absorb depth information and contact information, if the user is focused on the location 805 at which energy is applied. The gauge element 813 comprises a marker 814 which is similar to the marker 14 of the gauge element 13 described above with reference to FIG. 5.

Also the display 810 can display transmural regions as described above with reference to FIG. 5. If energy has been applied to all dots indicated in the first region 850 of the display 810 such that the lesions created at these locations are transmural, these dots have a color which, according to the gauge element 813, indicates that the lesions at the locations of these dots are transmural. For example, these dots can have a green color.

The white dots 880 shown in the second region 851 can be used for registering the electroanatomical map to a realtime fluoroscopy image. However, the second region 851 can also be adapted to not show these white dots. The first region 850 shows the catheter 21 and further elements 90, 91 present in the heart 3. In other embodiments, the further elements 90, 91 may not be present in the first region.

Referring again to FIG. 1 and FIG. 5, the visual property assigning unit 9, the display 10 with the gauge element 13 and the marker 14, and the transmural region calculation unit 15 form a visualization apparatus for visualizing a quality of applying energy to an object. This visualization apparatus has been described as being a part of the energy application apparatus 1. However, the visualization apparatus can also be a standalone system as schematically and exemplarily shown in FIG. 17.

Figure 17:
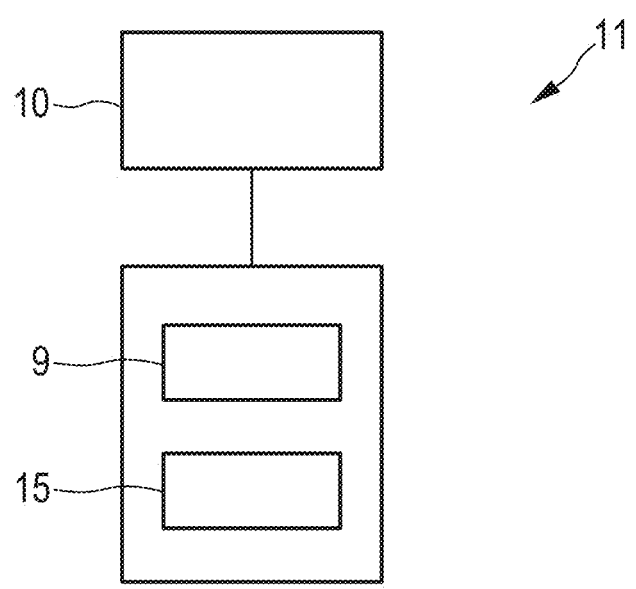
FIG. 17 shows schematically and exemplarily an embodiment of a visualization apparatus for visualizing a quality of applying energy to an object.

FIG. 17 shows a visualization apparatus 11 being adapted to visualize the quality of applying energy at a location on an object 3 based on a provided image of the object and a provided quality value at the location 5 on the object 3, wherein the quality value represents the quality of applying energy to the object at the location 5 on the object. In particular, the quality value is a depth value being indicative to the depth, to which the applied energy has altered the object 3 at the location 5, and/or a contact value being indicative of a degree of contact between the energy application element and the object. The visualization apparatus 11 comprises at least the visual property assigning unit 9 for assigning a visual property to the location at which energy is applied depending on the quality value and the display 10 for displaying the provided image and the assigned visual property at the location at which energy is applied on the object shown in the image. The visualization apparatus 11 preferentially further comprises the transmural region calculation unit 15 for calculating a transmural region of the object based on a provided depth value. The display 10 is preferentially adapted to show the calculated transmural region and the above mentioned gauge element.

Instead of the display 10 described above with reference to FIG. 5, the visualization apparatus 11 can comprise another display, for example, the display described above with reference to FIGS. 12 to 16.

Figure 18:
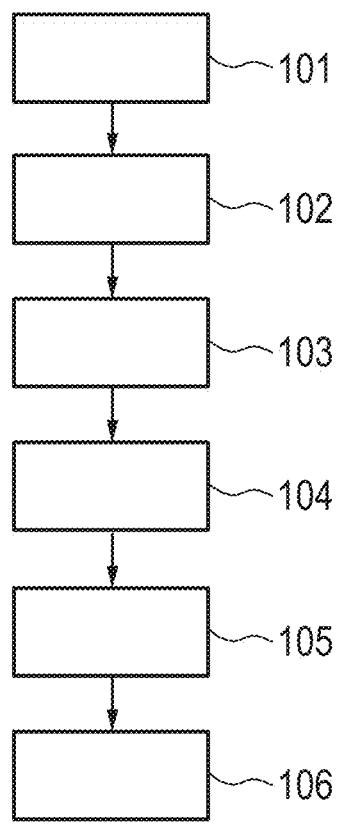
FIG. 18 shows a flowchart exemplarily illustrating an embodiment of an energy application method for applying energy to an object.

In the following an embodiment of an energy application method will exemplarily be described with reference to a flowchart shown in FIG. 18.

In step 101, an image of the object which is, in this embodiment, a heart 3 of a person 20 is provided by the image providing unit 2.

In step 102, an energy application element 4 being preferentially an ablation electrode of a catheter tip is localized for determining a location 5 of the energy application element 4 by the localizing unit 6, 7. The determined location 5 is preferentially shown in the display 10 or 810 with respect to the object 3. The energy application element 4 has preferentially already been navigated to the location 5, in order to apply energy to the object 3 at this location 5. However, if the determined location of the energy application element 4 does not correspond to a desired ablation site, the energy application element 4 can be navigated to the desired ablation site by using the navigation unit 29. During this navigation procedure and/or after the navigation procedure has been completed, the location of the energy application element 4 can be determined, in order to assist the user while navigating the energy application element to the desired ablation site and/or to verify whether the energy application element 4 has been navigated to the desired ablation site. If the determined location 5 coincides with the desired ablation site, in step 103 energy is applied to the object at the location 5 by using the localized energy application element 4.

In step 104, a quality value is determined at the location 5 on the object 3. For example, the depth value and/or the contact value are determined as quality value.

In step 105, a visual property is assigned to the location 5 depending on the quality value. In particular, a color is assigned to the location 5 depending on a depth value, and/or an intensity is signed to the location 5 depending on a contact value, and in step 106, the provided image and the assigned visual property at the location 5 on the object are shown in the provided image.

Steps 103 to 106 are preferentially performed repeatedly in order to visualize the actual quality value, in particular, the actual ablation depth and/or the actual contact value, in realtime. It should be noted that the sequence of steps 103 to 106 can be modified. For example, steps 104 to 106 can be performed before step 103.

Steps 105 and 106 can be regarded as the steps of a visualization method for visualizing a quality of applying energy to an object, wherein the visualization method is adapted to visualize the quality of applying energy at a location 5 on the object 3 based on a provided image 12 of the object 3 and a provided quality value at the location 5 on the object 3.

Atrial Fibrillation (AF) affects a significant fraction of the world's population, primarily the elderly. It is driven by triggers within the pulmonary veins. A well-accepted treatment method for AF patients is catheter ablation, in which a catheter is used to create a ring of electrically-dead scar tissue around the pulmonary vein, electrically isolating the triggers in the pulmonary veins from the atria. The catheter is typically localized using an electromagnetic localization system (e.g. CARTO or NavX) or the fluoroscopy-based Philips EP Navigator. These systems can in addition use a single-point electrode at the tip of the catheter to sequentially acquire contact electrograms and display this data as an electroanatomic map to assist in treatment planning. In addition, points at which ablation energy has been developed or at which diagnostic-value electrograms have been collected, are marked on the electroanatomic map. An electroanatomic map with these features can be displayed by the display of the energy application apparatus and the visualization apparatus. In addition, the display shows the visual property assigned to a location at which energy is applied depending on a provided quality value, in particular, the provided depth value, at the location on the electroanatomic map at which energy is applied. Moreover, as already mentioned above, the display preferentially also shows the gauge element with the marker and the calculated transmural region.

The pulmonary veins must be completely electrically isolated from the atrium for long-term success i.e. not only must the lesion set must be continuous, but also each lesion must be completely transmural. However, if ablation energy is delivered too deeply or for too long the risk of morbidity and mortality due to tamponade (cardiac perforation) or stroke is significantly increased. Furthermore, the thickness of the atrial wall differs significantly between patients, and between different areas in a patient's atrium. Therefore, catheter ablation of atrial fibrillation is a difficult and risky procedure to conduct; since electrophysiologists wish to minimize patient complications, they often create lesions that are too shallow and as a result as many as 40% of AF ablation procedures are not successful in the long-term.

The energy application apparatus and the visualization apparatus can provide electrophysiologists with a tool that displays ablation depth in realtime to allow them to determine how long to ablate at each location. This can increase the efficiency and efficacy with which catheter ablation of AF is conducted, and reduce the risk of patient complications. The depth information can be displayed in such a way that it blends seamlessly with a standard visualization system, i.e. an extra display is preferentially not required. Furthermore, the visualization of the depth value does preferentially not disturb current clinical workflow, since the ablation depth information is displayed exactly at the location on the image at which electrophysiologists will normally be focused during application of ablation energy, i.e. on the realtime image of the catheter tip. The visualization of the depth information, and preferentially also of the contact information, in accordance with the invention can therefore be integrated into existing ablation monitoring displays like the Philips EP navigator system.

The energy application apparatus and visualization apparatus can be applied to the treatment planning of catheter or surgical ablation of, for example, cardiac arrhythmias, tumors, et cetera. A particularly important cardiac application is atrial and ventricular arrhythmias and specifically the treatment of atrial fibrillation or ventricular tachycardia. The energy application apparatus and the visualization apparatus can also be used in other applications, for example, in applications for applying energy to a technical object or for a realtime treatment assessment of the heart or other organs in oncology.

Although in the above described embodiments a cardiac catheter ablation is performed, the visualization apparatus can also be adapted to visualize the quality of applying another kind of energy to another object and the energy application apparatus can be adapted to apply another kind of energy to another object. For example, instead of RF energy optical energy, heat, coldness, acoustical energy, nuclear energy, et cetera, can be applied to the object. Moreover, the object can be another organ of a person not being the heart like the liver, the lung, the kidney, et cetera. The object can also be a technical object. The visualization apparatus can also be adapted to monitor a surgical ablation procedure.

The visualization apparatus and/or the energy application apparatus can be adapted to allow a physician to color-code a dot on the display based on his subjective assessment of the M-mode image, after the application of energy has been completed. For example, they can be adapted to allow a physician to assign a green color to a dot at a location at which the lesion is completely transmural, to assign an orange color to a dot at a location at which the lesion is only partially transmural and to assign a red color to a dot at a location at which there is no lesion at all or the degree of transmurality is smaller than 10%. Thus, the visualization apparatus and/or at which energy application apparatus can comprise an input unit like a keyboard or a mouse allowing a physician to color code the dots on the display based on his subjective assessment. In a further embodiment, the visualization apparatus and energy application apparatus can be adapted for marking desired locations, at which energy should be applied, and for color coding for multi-point devices, wherein the energy application element is adapted to apply energy at different points simultaneously or consecutively.

The visualization apparatus and/or energy application apparatus can comprise a storing unit for storing ultrasound data like an M-mode image or information, which has been obtained based on an ultrasound signal like lesion depth, tissue contact, slippage, tissue pop, thickness, and/or other physiological data like impedance, temperature, power, electrograms, optical properties of tissue surface, et cetera. This information is, for example, recorded before and/or during and/or after applying energy to the object and linked to the respective dot at the location to which the stored information belongs. The visualization apparatus and/or the energy application apparatus can comprise an input unit like a keyboard or a mouse for selecting a dot on the display and, if a certain dot has been selected, the information assigned to the selected dot is provided to the user, for example, in a pop-up window.

The energy application apparatus can further comprise a tissue pop detection unit for detecting tissue pops, wherein the visualization apparatus is adapted to show a detected tissue pop to a user, for example, by modifying the visual property of the entire display or of one or several dots shown on the display. For example, one or several dots can blink or a flash can be shown, if a tissue pop has been detected.

Although in the embodiment described above with reference to FIG. 5 the display comprises three regions and in the embodiment described above with reference to FIGS. 12 to 14 and 16 the display comprises five regions, the display can also comprise another number of regions. In particular, the display can only comprise the first region or only the second region.

Although in the embodiment described above with reference to FIGS. 2 to 4 the depth value, in particular, the ablation depth, has been determined from ultrasound signals, the depth value can also be determined by using other methods. For example, the depth value can optically be determined as disclosed in the above mentioned US 2006/0122587 A1, or the depth value can be determined based on magnetic resonance signals.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Calculations and determinations like the determination and calculation of the quality value and the transmural region and the assignment of a visual property performed by one or several units or devices can be performed by any other number of units or devices. For example, steps 101, 104 and 105 can be performed by a single unit or by any other number of different units. The calculations, determinations, assignments et cetera and/or the control of the visualization apparatus in accordance with the visualization method and/or the control of the energy application apparatus in accordance with the energy application method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a visualization apparatus for visualizing a quality of applying energy to an object. The quality of applying energy at a location on the object is visualized based on a) a provided image of the object and b) a provided quality value representing the quality of applying energy to the object at the location on the object, wherein a visual property assigning unit assigns a visual property to the location depending on the quality value and a display displays the provided image and the assigned visual property at the location on the object shown in the image. In general a person who applies energy to the object is focused on the location at which energy is applied. Since quality information is shown at the location on which the person is already focused, the quality dependent information can easily be absorbed by the person.

The invention claimed is:

1. A visualization apparatus for visualizing a quality of applying energy to an object, wherein the visualization apparatus is adapted to visualize the quality of applying energy at a location on the object based on a provided image of the object and a provided quality value representing the quality of applying energy to the object at the location on the object, wherein the quality value is a depth value being indicative of the depth to which the applied energy has altered the object at the location, wherein the visualization apparatus comprises:
   a visualization property assigning unit for assigning a visual property to the location depending on the quality value, and
   a display for displaying the provided image and the assigned visual property at the location on the provided image,
   wherein the depth value is provided with respect to a thickness of a wall of the object to which the energy is applied, wherein the visualization apparatus further comprises a transmural region calculation unit for calculating a transmural region of the object based on the provided depth value and wherein the display is adapted to show the calculated transmural region on the image of the object, wherein the transmural region calculation unit is adapted to calculate the transmural region by using several depth values, which are provided for several locations, and by using the locations for which the several values have been provided.

2. The visualization apparatus as defined in claim 1, wherein energy is applied to the object by using an energy application element and wherein a further quality value being a contact value is provided, wherein the contact value is indicative of a degree of contact between the energy application element and the object, wherein the visual property assigning unit is adapted to assign one of the color and the intensity to the location depending on the depth value and the other of the color and the intensity to the location depending on the contact value, wherein the display is adapted to display the assigned color and the assigned intensity at the location on the provided image.

3. The visualization apparatus as defined in claim 1, wherein the provided image of the object is an anatomic map of the object and wherein the display is adapted to display the assigned visual property at the location on the anatomic map.

4. The visualization apparatus as defined in claim 1, wherein the visualization apparatus further comprises a gauge element shown on the display, wherein the gauge element is adapted to indicate a relation between the visual property and the quality value.

5. The visualization apparatus as defined in claim 4, wherein the gauge element comprises a marker indicating the depth to which the applied energy has altered the object based on the provided depth value.

6. The visualization apparatus as defined in claim 1, wherein the quality value is repeatedly provided during applying energy to the object, wherein the visual property assigning unit is adapted to repeatedly assign a visual property to the location depending on the respective actually provided quality value and wherein the display is adapted to repeatedly display the provided image and the respective actually assigned visual property at the location on the object shown in the image.

7. An energy application apparatus for applying energy to an object, the energy application apparatus comprising:
an image providing unit for providing an image of the object,
an energy application element for applying the energy to the object at a location,
a localization unit for localizing the energy application element at the location,
a sensing unit for generating an ultrasound signal being indicative of a property of the object,
a quality value determination unit for determining a quality value at the location on the object, wherein the quality value represents the quality of applying energy to the object at the location, wherein the quality value is a depth value being indicative of the depth to which the applied energy has altered the object at the location,
the visualization apparatus as defined in claim 1.

8. A visualization method for visualizing a quality of applying energy to an object, wherein the visualization method is adapted to visualize the quality of applying energy at a location on the object based on a provided image of the object and a provided quality value at the location on the object, the quality value representing the quality of applying energy to the object at the location on the object, wherein the quality value is a depth value being indicative of the depth to which the applied energy has altered the object at the location, wherein the visualization method comprises:
assigning a visual property to the location depending on the quality value,
displaying the provided image and the assigned visual property at the location on the provided image,
wherein several depth values are provided for several locations with respect to a thickness of a wall of the object to which the energy has been applied, wherein a transmural region of the object is calculated by using the several depth values, which are provided for the several locations, and by using the several locations for which the several depth values have been provided and wherein the calculated transmural region is displayed on the image of the object.

9. A computer program product for visualizing an effect of applying energy to an object, wherein the computer program product comprises program code encoded on a non-transitory computer readable medium for causing a visualization apparatus as defined in claim 1 to carry out the steps of a visualization method when the computer program code is executed by a computer controlling the visualization apparatus, the visualization method comprising the steps of:
assigning a visual property to the location depending on the quality value,
displaying the provided image and the assigned visual property at the location on the provided image,
wherein several depth values are provided for several locations with respect to a thickness of a wall of the object to which the energy has been applied, wherein a transmural region of the object is calculated by using the several depth values, which are provided for the several locations, and by using the several locations for which the several depth values have been provided and wherein the calculated transmural region is displayed on the image of the object.

10. A computer program product for applying energy to an object, wherein the computer program product comprises program code encoded on a non-transitory computer readable medium for causing an energy application apparatus as defined in claim 7 to carry out the following steps, when the program code is executed by a computer controlling the energy application apparatus:
providing an image of the object,
localizing an energy application element for determining a location of the energy application element,
applying energy to the object at the location by using the localized energy application element, and
determining a quality value at the location on the object, wherein the quality value represents the quality of applying energy to the object at the location, wherein the quality value is a depth value being indicative of the depth to which the applied energy has altered the object at the location,
wherein computer program further comprises a computer program for visualizing an effect of applying energy to an object as defined in claim 9.

\* \* \* \* \*